US007645446B2

(12) United States Patent
During et al.

(10) Patent No.: US 7,645,446 B2
(45) Date of Patent: *Jan. 12, 2010

(54) GLUTAMIC ACID DECARBOXYLASE (GAD) BASED DELIVERY SYSTEM

(75) Inventors: Matthew During, New York, NY (US); Michael Kaplitt, New York, NY (US)

(73) Assignee: Neurologix, Inc., Fort Lee, NJ (US)

( * ) Notice: Subject to any disclaimer, the term of this patent is extended or adjusted under 35 U.S.C. 154(b) by 293 days.

This patent is subject to a terminal disclaimer.

(21) Appl. No.: 10/802,417

(22) Filed: Mar. 16, 2004

(65) Prior Publication Data

US 2006/0099179 A1   May 11, 2006

Related U.S. Application Data

(63) Continuation of application No. 09/863,179, filed on May 23, 2001, now Pat. No. 6,780,409.

(60) Provisional application No. 60/206,281, filed on May 23, 2000.

(51) Int. Cl.
*A01N 63/00* (2006.01)
*A01N 65/00* (2009.01)
*A61K 48/00* (2006.01)

(52) U.S. Cl. .................................... 424/93.2; 424/93.1
(58) Field of Classification Search ................ 424/93.1, 424/93.2
See application file for complete search history.

(56) References Cited

U.S. PATENT DOCUMENTS

| 5,187,162 A | 2/1993 | Marangos et al. |
| 5,681,744 A | 10/1997 | Greenstein |
| 6,180,613 B1 * | 1/2001 | Kaplitt et al. ................ 514/44 |
| 6,682,906 B1 | 1/2004 | Tobin et al. |
| 6,780,409 B2 * | 8/2004 | During et al. ............. 424/93.2 |
| 2004/0101514 A1 | 5/2004 | Liu et al. |

FOREIGN PATENT DOCUMENTS

WO    WO 95/25805    9/1995

OTHER PUBLICATIONS

Crystal (1995) Transfer of genes to humans: Early lessons and obstacles to success. Science 270: 404-410.*
Deonarain (1998) Ligand-targeted receptor-mediated vectors for gene delivery. Exp. Opin. Ther. Patents 8(1): 53-69.*
Friedmann (1997) Overcoming the obstacles to gene therapy. Scientific American, Jun. 1997, pp. 97-101.*
Miller et al. (1995) Targeted vectors for gene therapy. FASEB J. 9: 190-199.*
Orkin and Motulsky (1995) Report and recommendations of the panel to assess the NIH investment in research on gene therapy. pp. 1-40.*
Ross et al. (1996) Gene therapy in the United States: A five year status report. Human Gene Therapy 7: 1781-1790.*
Rubanyi (2001) The future of human gene therapy. Mol. Aspects Med. 22: 113-142.*
Thomas (2003) Progress and problems with the use of viral vectors for gene therapy. Nature Reviews Genetics 4: 346-358.*
Verma et al. (1997) Gene therapy—promises, problems and prospects. Nature 389: 239-242.*
Bu et al., "Two Human Glutamate Decarboxylases, 65-kDa GAD and 67-kDa GAD, Are Each Encoded by a Single Gene," *Proc. Natl. Acad. Sci. USA*, vol. 89, 2115-2119 (Mar. 1992).
Cao et al., "High-Titer, Wild-Type Free Recombinant Adeno-Associated Virus Vector Production Using Intron-Containing Helper Plasmids," *Journal of Virology*, vol. 74, No. 24, 11456-11463 (Dec. 2000).
Celada et al., "Gabaergic Control of Rat Substantia Nigra Dopaminergic Neurons: Role of Globus Pallidus and Substantia Nigra Pars Reticulata," *Neuroscience*, vol. 89, No. 3, 813-825 (1999).
During at al., "Peroral Gene Therapy of Lactose Intolerance Using an Adeno-Associated Virus Vector," *Nature Medicine*, vol. 4, No. 10 (Oct. 1998).
Kotin, Robert M., "Prospects for the Use of Adeno-Associated Virus as a Vector for Human Gene Therapy," *Human Gene Therapy*, vol. 5, 793-801 (1994).
Linderfors, Nils, "Dopaminergic Regulation of Glutamic Acid Decarboxylase mRNA Expression and GABA Release in the Striatum: A Review," *Prog. Neuro-Psychopharmacol & Biol. Psychiatry*, vol. 17, 887-903 (1993).
Martin et al., "Are $GAD_{65}$ and $GAD_{67}$ Associated with Specific Pools of GABA in Brain?" *Perspectives on Developmental Neurobiology*, vol. 5, 119-129 (1998).
Miller et al., "The Central Medial Necleus: Thalamic Site of Seizure Regulation," *Brain Research*, vol. 508, 297-300 (1990).
Schenk et al., "Immunization with Amyloid-β Attenuates Alzheimer-Disease-Like Pathology in the PDAPP Mouse," *Nature*, vol. 400, 173-177 (Jul. 1999).
Veliskova at al., "Subthalamic Nucleus: A New Anticonvulsant Site in the Brain," *Neuroreport*, vol. 7, No. 11, 1786-1788 (1996); and.
Xu et al., "Is the Anticonvulsant Effect of Substantia Nigra Infusion of Gama-Vinyl-GABA (GVG) Mediated by the $GABA_A$ Receptor in Rat Pups?" *Developmental Brain Research*, vol. 59, 17-21 (1991).
Robert, JJ et al. "Adenovirus-Mediated Transfer of a Functional GAD Gene Into Nerve Cells: Potential For The Treatment of neurological Diseases" Gene Therapy, vol. 4, No. 11, pp. 1237-1245 (1997).
Mi, Jie et al. "Recombinant Aden-Associated Virus (AAV) Drives Constitutive Production of Glutamate Decarboxylase In Neural Cell Lines" Journal of Neuroscience Research, vol. 57, pp. 137-148 (1999).
New, Kent et al. "Novel Synthesis and Release of GABA In Cerebellar Granule Cell Cultures After Infection With Defective Herpes Simplex Virus Vectors Expressing Glutamic Acid Decarboxylase" Molecular Brain Research, Vol., pp. 121-135 (1998).
Navarro, V. et al. "Efficient Gene Transfer and Long-Term Expression in Neurons Using A Recombinant Adenovirus With A neuron-Specific Promoter" Gene Therapy, vol. 6, pp. 1884-1892 (1999).

* cited by examiner

*Primary Examiner*—Anne-Marie Falk
(74) *Attorney, Agent, or Firm*—Nutter McClennen & Fish LLP; George A. Xixis

(57) ABSTRACT

The invention provide methods and compositions for localized delivery of a vector comprising a therapeutic agent to a specific region of the brain that is overstimulated in neurodegenerative diseases. In particular, the invention provides methods and compositions used to deliver an adeno-associated virus vector (AAV) comprising a nucleotide sequence encoding glutamic acid decarboxylase (GAD) to cells in the subthalmic nucleus of the basal ganglia, mesaphilia and thalamus.

8 Claims, 21 Drawing Sheets

FIG. 2A
FIG. 2B
FIG. 2C
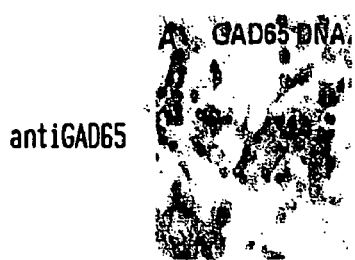
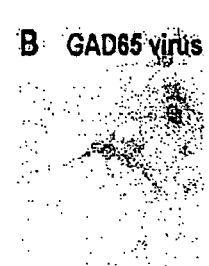
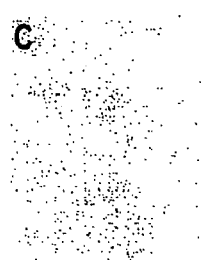
FIG. 2D
FIG. 2E
FIG. 2F

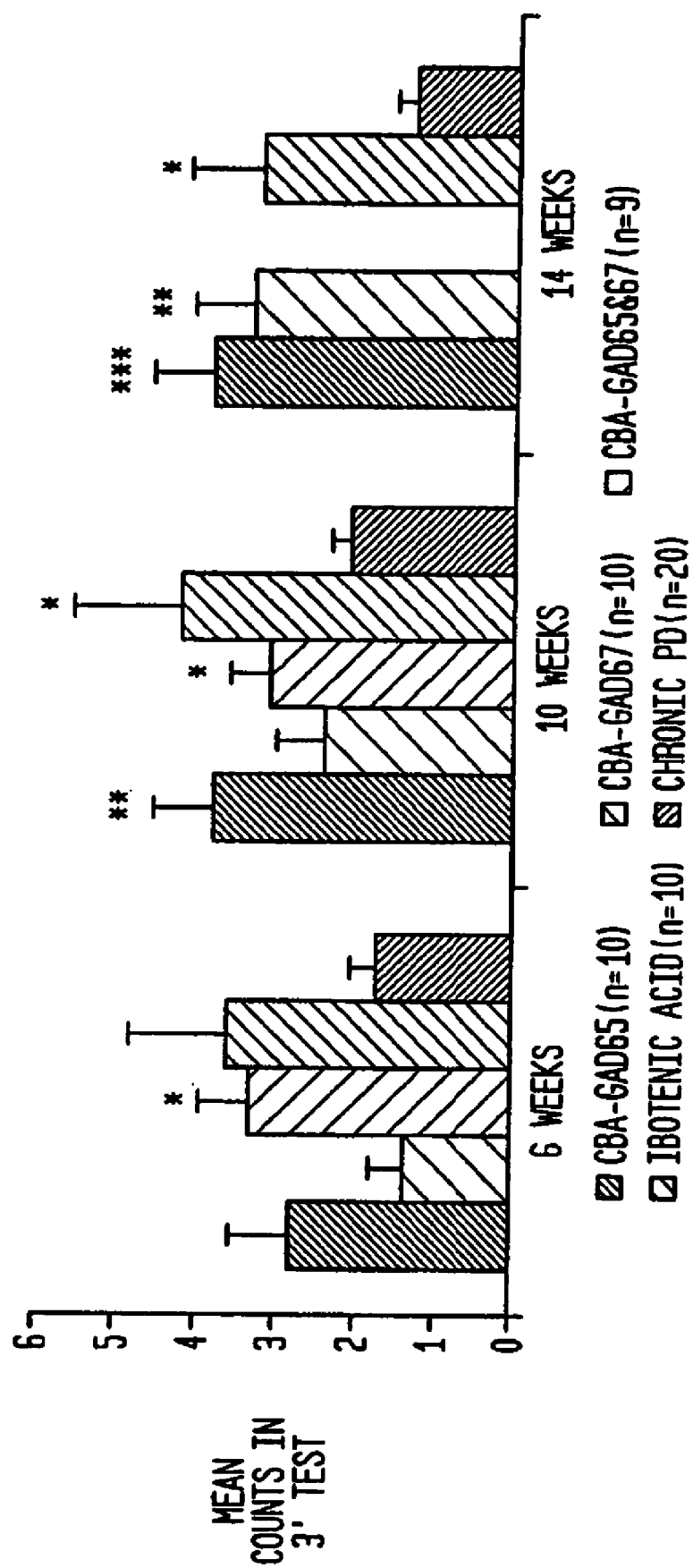

GLUTAMIC ACID DECARBOXYLASE (GAD) BASED DELIVERY SYSTEM

This application claims priority to U.S. Provisional Patent Application Ser. No. 60/206,281, filed May 23, 2000, and is a continuation of U.S. patent application Ser. No. 09/863,179, filed May 23, 2001, which are incorporated by reference.

BACKGROUND OF THE INVENTION

The invention is generally in the field of methods and compositions for treating neurodegenerative diseases such as Parkinson's disease, using viral and non-viral delivery systems that deliver therapeutic agents to specific regions of the brain. More specifically, using an adeno-associated viral vector to deliver a nucleotide sequence encoding glutamic acid decarboxylase (GAD) to specific regions of the brain that are overstimulated or disinhibited in neurodegenerative diseases.

The major inhibitory neurotransmitter in the brain is gamma-aminobutyric acid (GABA), (Roberts et al, GABA in Nervous System Function, Raven Press: New York, 1976; McGeer E G, et al, Glutamine, Glutamate, and GABA in the Central Nervous System; Hertz L, Kvamme E, McGeer E G, Schousbal A, eds., Liss: New York, 1983;3-17). Loss of GABA signaling, by a reduction in release, loss of neurons which synthesize GABA, or antagonism of GABA receptors leads to disinhibition, overexcitation and depending on the specific brain region involved, may result in epilepsy, movement disorders or other neurological deficits and symptoms.

Diseases such as Parkinson's disease, Huntington's disease, Amyotrophic Lateral Sclerosis (ALS or Lou Gehrig's Disease), Epilepsy and Alzheimer's disease, have proved difficult to treat. Few, if any therapies, have proved effective in slowing or arresting the degenerative process associated with these diseases. In Parkinson's Disease (PD), the primary neurochemical disturbance is believed to be the loss of substantia nigra (SN) dopaminergic (DA) neurons. This loss of DA neurons leads to a profound deficit of DA in the projection areas of the caudate and putamen and results in a loss of signaling through dopamine receptors in the postsynaptic neurons. These neurons, via efferents referred to as the direct and indirect pathways, synapse on other cells in the basal ganglia circuitry. Of most relevance to PD, the loss of dopamine receptors in the basal ganglia circuitry leads to loss of drive in the GABAergic inhibitory input to the subthalamic nucleus.

The loss of inhibitory GABAergic drive to the subthalmic nucleus (STN) results in increased activity of the STN which sends excitatory (glutamatergic) afferents to the ventral media (VM) thalamus, the substantia nigra pars reticulata (SNPR) and a lesser projection to the pars compacta, as well as other cells within the basal ganglia including the globus pallidus. When the concentration of GABA diminishes below a threshold level in the brain, movement disorders and convulsions may result (See e.g., Karlsson et al, (1974) *Biochem. Pharmacol* 23:3053-3061). GABA synthesis is regulated by glutamic acid decarboxylase (GAD). GAD is present in the brain as two isoforms, GAD-65 and GAD-67. When the GABA levels rise in the brain the convulsions terminate (See e.g., Hayashi (1959) *Physiol.* 145:570-578). In convulsive disorders, the reduction in brain GABA levels is often paralleled by a diminished level of GAD (McGeer, et al. GABA in Nervous System Function; Roberts E, Chase T N, Tower D B, eds., Raven Press: New York 1976:487-495; Butterworth et al. (1983) *Neurochem.* 41:440-447; Spokes et al. (1978) *Adv. Exp. Med. Biol.* 123:461-473).

Levodopa (L-dopa) has historically been the medication of choice to treat Parkinson's disease. L-dopa is a precursor to dopamine and is able to cross the blood-brain barrier to target the brain. In order to reduce the global effects of L-dopa, it is often given with carbidopa, a peripheral decarboxylase inhibitor which decreases the metabolism of L-dopa in the peripheral tissues. Unfortunately, the response with L-dopa is not sustainable. Most patients develop adverse effects after long-term usage of L-dopa, and often the benefits of treatment wane as the disease progresses. In addition, several common types of central nervous system dysfunction and peripheral side effects are associated with administration of L-dopa. Toxic side effects to the central nervous system include mental changes, such as confusion, agitation, hallucinations, delusions, depression, mania and excessive sleeping. In addition, L-dopa can exacerbate malignant melanomas or other skin lesions and can have untoward effects in patients with cardiovascular or pulmonary disease, asthma, or renal, hepatic or endocrine disease.

Other methods for treating Parkinson's disease include transplantation of cells used to repair regions of the brain damaged by neurodegeneration. These cells can be engineered to secrete neuroactive substances such as L-dopa. The procedure typically involves cell transplantation into the stratium. Repair of the damaged regions and secretion of L-dopa depends on the transplanted cells being able to re-establish synaptic connections with several structures situated at a considerable distance from the area of neurodegeneration. However, cell transplantation is a complicated procedure which requires donor tissue, and there have been reports of mortality associated with this procedure.

Alternative forms of treating Parkinson's disease involve implanting devices for deep-brain stimulation (DBS) in specific regions of the brain. For example, DBS of the STN. These devices are typically electrodes implanted into the STN. The electrode is then stimulated at a desired frequency to reduce the effect of Parkinson's disease. The significance of the STN overactivity is reflected in the success of ablative surgery of the STN in both animal models of Parkinson's disease, as well as in human Parkinson's disease itself. In addition to ablation, implantation of nedtronic stimulators are commonly employed. The mechanism of the stimulators is believed to be mediated by local inhibition (via GABA signaling), and is replicated by the local infusion of GABA agonists.

Each of these approaches, surgical ablation, electrical stimulation and infusion of pharmacological GABA agonists is effective in disease palliation, but each has significant adverse effects. For example, extensive invasive surgery, a high risk of infection and potential damage to the brain and in the case of drug infusion, very transient efficiency.

Thus, the treatments for neurodegenerative disorders are palliative at best, with limited and transient efficacy. Therefore, a need exists for a therapeutic approach which has advantages in targeting specificity, both short and long-term efficacy, as well as neuroprotection, without extensive surgery or side-effects.

SUMMARY OF THE INVENTION

The invention is based, at least in part, on the discovery that localized delivery of a vector comprising a therapeutic agent to a specific region of the brain that is overstimulated or disinhibited in neurodegenerative diseases, can reduce the effect of overstimulation and promote the improvement of the neurodegenerative disease. In particular, the invention pertains to methods and compositions used to deliver a vector, (e.g., an adeno-associated virus vector (AAV)) comprising a nucleotide sequence encoding glutamic acid decarboxylase (GAD) to target cells, e.g., the subthalmic nucleus of the basal ganglia.

Particularly preferred methods of delivering the vector to specific regions of the brain are those techniques that are simple, safe, and have a lower risk associated with them than lesioning, electrode implantation or cell transplantation. For example, delivery of the vector using stereotactic microinjection techniques, or delivery of the vector using specialized probes, or percutaneous delivery via disruption of the blood-brain barrier. Delivery of the vector using the method of the invention results in minimal immunological or inflammatory responses within the regions of the brain, thus eliminating the need for immunosupression. After delivery of the vector to a specific region of the brain, regional dispersion and/or diffusion of vector occurs ensuring local distribution of gene and stable gene expression.

The methods and compositions are particularly useful for treating neurodegenerative diseases, such as Parkinson's disease, Huntington's disease, Amyotrophic Lateral Sclerosis (ALS or Lou Gehrig's Disease), Alzheimer's Disease as well as epilepsy.

Accordingly, in one aspect, the invention features a method for treating or reducing a neurodegenerative disease in a subject comprising:

identifying a target site in the central nervous system that requires modification;

delivering a vector comprising a nucleotide sequence encoding a glutamic acid decarboxylase (GAD) to the target site in the central nervous system; and expressing the GAD in the target site in an amount effective to treat or reduce the neurodegenerative disease.

In one embodiment, the vector is a viral vector, and is selected form the group consisting of adenovirus vectors, herpes virus vectors, parvovirus vectors, and lentivirus vectors. In a preferred embodiment, the viral vector is an adeno-associated viral vector.

In another embodiment, the vector is a non-viral vector. In a preferred embodiment, the non-viral vector is a liposome-mediated delivery vector.

In one embodiment, the vector is delivered to a specific target site of the central nervous system. In a preferred embodiment, the vector is delivered using stereotaxic delivery, or delivery using specialized probes. In a preferred embodiment, the target site of the central nervous system is a region of the brain. In another preferred embodiment, the region of the brain is selected from the group consisting of basal ganglia, subthalmic nucleus (STN), pedunculopontine nucleus (PPN), substantia nigra (SN), thalamus, hippocampus, cortex and combinations thereof. In a more preferred embodiment, the region of brain is the subthalmic nucleus (STN).

In one embodiment, the neurodegenerative disease is selected from the group consisting of Parkinson's disease and related movement disorders, Alzheimer's disease, senile dementia, Amyloid Lateral Sclerosis (ALS), and epilepsy.

In another aspect, the invention features a method for treating or reducing a Parkinson's disease in a subject comprising:

identifying one or more regions of the brain that require modification;

delivering a vector comprising a nucleotide sequence encoding a glutamic acid decarboxylase (GAD) to the region of the brain; and expressing the GAD in the region of the brain an amount effective to treat or reduce Parkinson's disease.

In yet another aspect, the invention features a vector for expression of GAD in cells of the central nervous system comprising a tissue specific promoter operably linked to a nucleic acid encoding GAD, and a post-transcriptional regulatory element.

In one embodiment, the promoter is specific for central nervous system cells and tissues, such as the cells and tissues of the brain. In a preferred embodiment, the promoter is the neuron specific enolase (NSE) promoter.

The vector also preferably comprises post-transcriptional regulatory elements to enhance expression of the encoded protein. In a preferred embodiment, the post-transcriptional regulatory element is the woodchuck post-transcriptional regulatory element. In another preferred embodiment, the GAD is selected from the group consisting of GAD-65 and GAD-67.

BRIEF DESCRIPTION OF FIGURES

FIGS. 2A-2F are microphotographs showing plasmid transfection according to the invention; FIGURES A and D show plasmid transfection of HEK 293 cells with 1 µg of rAAV DNA and FIGURES B and E. show rAAV vector transduction of HEK 293 cells with 5 µl rAAV vector while FIGURES C and F. show non-transfected HEK 293 cells.

FIG. 11 is a further graph showing that rAAV-GAD-65 had a marked neuroprotective effect on paw touching counts.

FIGS. 19A,B,C, and D show GAD65 expression in the STN detected with GAD65 Ab (Boehringer). FIGS. 19A and C are derived from naïve STN, showing endogenous GAD65 expression. FIGS. 19B and D are based on rAAV-GAD65 transduced STN, such that an increase in cell bodies expressing GAD65 is seen, while FIGS. 19 E and F show GAD65 expression in the hippocampus. (FIG. 19E being naïve and FIG. 19F being rAAV-GAD65 transduced);

DETAILED DESCRIPTION

Figure 1:
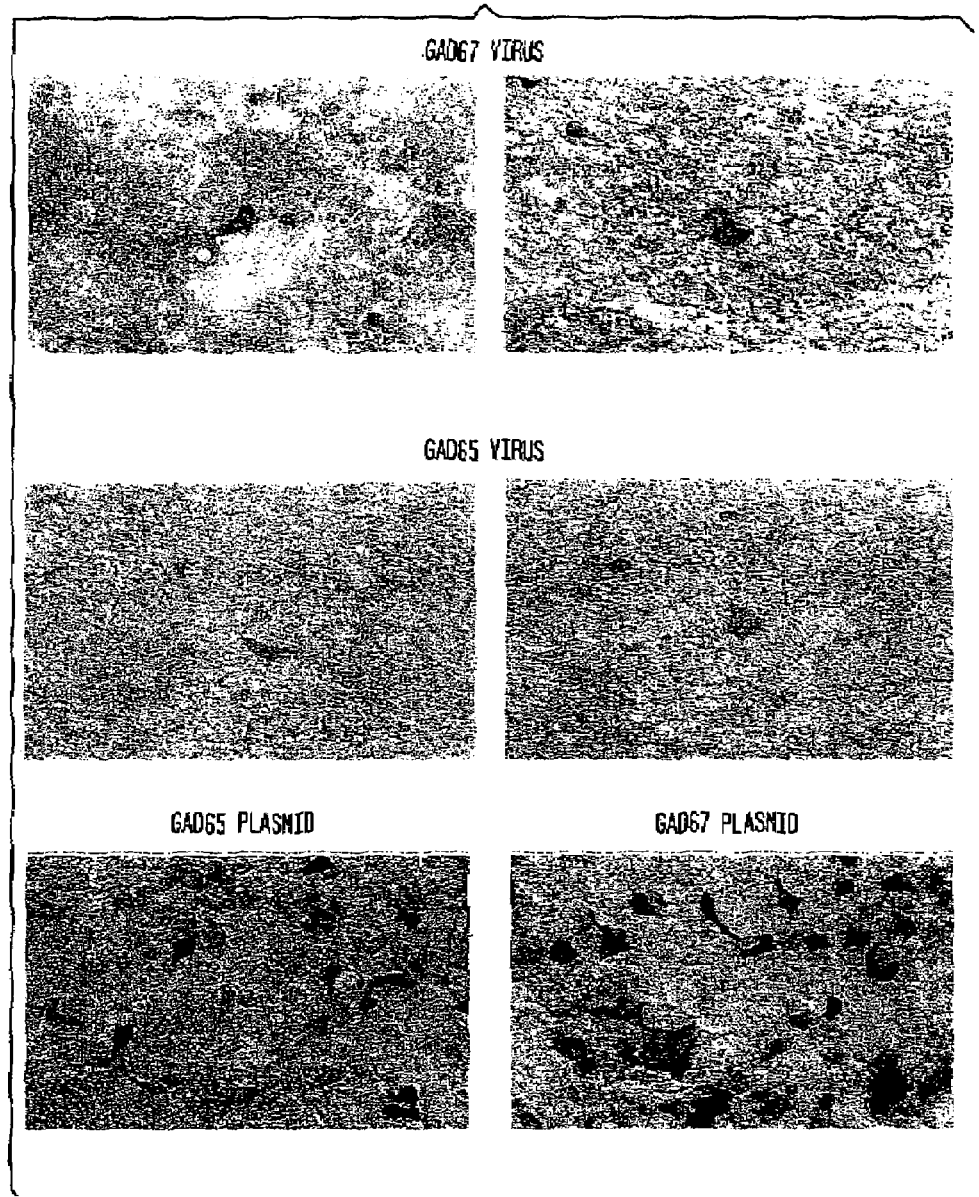
FIG. 1 shows images of in primary neuronal cultures from the subthalamic nucleus infected with AAV virus vectors expressing GAD-67 (top two panels), or virus vectors expressing GAD-65 (middle two panels). The bottom two panels show cells infected with the GAD-65 plasmid (left bottom panel) and the GAD-67 plasmid (right bottom panel).

The practice of the present invention employs, unless otherwise indicated, conventional methods of virology, microbiology, molecular biology and recombinant DNA techniques within the skill of the art. Such techniques are explained fully in the literature. (See, e.g., Sambrook, et al. Molecular Cloning: A Laboratory Manual (Current Edition); DNA Cloning: A Practical Approach, Vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition); CRC Handbook of Parvoviruses, Vol. I & II (P. Tijessen, ed.); Fundamental Virology, 2nd Edition, Vol. I & II (B. N. Fields and D. M. Knipe, eds.))

So that the invention is more clearly understood, the following terms are defined:

The term "neurodegenerative disorder" as used herein refers to a disorder which causes morphological and/or functional abnormality of a neural cell or a population of neural cells. The neurodegenerative disorder can result in an impairment or absence of a normal neurological function or presence of an abnormal neurological function in a subject. For example, neurodegenerative disorders can be the result of disease, injury, and/or aging. Non-limiting examples of morphological and functional abnormalities include physical deterioration and/or death of neural cells, abnormal growth patterns of neural cells, abnormalities in the physical connection between neural cells, under- or over production of a substance or substances, e.g., a neurotransmitter, by neural cells, failure of neural cells to produce a substance or substances which it normally produces, production of substances, e.g., neurotransmitters, and/or transmission of electrical impulses in abnormal patterns or at abnormal times. Neurodegeneration can occur in any area of the brain of a subject and is seen with many disorders including, for example, head trauma, stroke, ALS, multiple sclerosis, Huntington's disease, Parkinson's disease, and Alzheimer's disease.

The term "subject" as used herein refers to any living organism in which an immune response is elicited. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered. The term "central nervous system" or "CNS" as used herein refers to the art recognized use of the term. The CNS pertains to the brain, cranial nerves and spinal cord. The CNS also comprises the cerebrospinal fluid, which fills the ventricles of the brain and the central canal of the spinal cord.

The term "modifies" or "modified" are used interchangeably herein and refer to the up-regulation or down-regulation of a target gene or a target protein. The term modifies or modified also refers to the increase, decrease, elevation, or depression of processes or signal transduction cascades involving a target gene or a target protein. For example, a target protein can be a GABA. Modification to the GABA concentrations may occur when a therapeutic agent, e.g., GAD, alters GABA concentration. For example, modifications that result in an increase in GABA concentration by the expression of GAD in glutaminergic neurons and intrinsic cells of the STN.

Modifications can also result from the addition of a therapeutic agent that inactivates GABA aminotransferase. The effect is to block the degradation of GABA and thereby increase its concentration. Numerous mechanism-based inactivators of GABA aminotransferase are known (See e.g., Silverman Mechanism-Based Enzyme Inactivation: Chemistry and Enzymology, Vol. I and II, CRC: Boca Raton 1988). The term modifies also includes increasing, or activating GAD with therapeutic agents that activate GAD, such as sodium valporate. The increase in GAD results in an increase in GABA, which subsequently reduces overstimulation of basal ganglia circuits.

Non-limiting examples of modifications includes modifications of morphological and functional processes, under- or over production or expression of a substance or substances, e.g., a neurotransmitter, by neural cells, failure of neural cells to produce a substance or substances which it normally produces, production of substances, e.g., neurotransmitters, and/or transmission of electrical impulses.

The term "tissue-specific promoter" as used herein refers to a promoter that is operable in cells of the central nervous system (CNS). Examples of promoters for the CNS include but are not limited to, neuron-specific promoters (e.g., the neurofilament promoter; Byrne and Ruddle (1989) *Proc. Natl. Acad. Sci. USA* 86:5473-5477) and glial specific promoters (Morii et al. (1991) *Biochem. Biophys Res. Commun.*

175: 185-191). Preferably, the promoter is tissue specific and is essentially not active outside the central nervous system, or the activity of the promoter is higher in the central nervous system that in other systems. For example, a promoter specific for the spinal cord, brainstem, (medulla, pons, and midbrain), cerebellum, diencephalon (thalamus, hypothalamus), telencephalon (corpus stratium, cerebral cortex, or within the cortex, the occipital, temporal, parietal or frontal lobes), STN, SN, or combinations, thereof. The promoter may also be one that can be used in combination with an AAV to result in higher expression. For example, a cytomegalovirus enhncer/chicken-Actin (CBA) hybrid promoter that functions in cenll of the CNS (Xu et al. (2001) *Hum Gene Ther.* 12:563-73).

The term "homology" or "identity" as used herein refers to the percentage of likeness between nucleic acid molecules. To determine the homology or percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. For example, the percent identity between two amino acid sequences can be determined using the Needleman and Wunsch ((1970) *J. Mol. Biol.* (48):444-453) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In another example, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In yet another example, the percent identity between two amino acid or nucleotide sequences is determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty.

The invention is described in more detail in the following subsections:

I. Neurodegenerative Diseases (a) Parkinson's Disease

Parkinson's disease is associated with a disturbances of posture, locomotion, facial expression or speech. The manifestations may be asymmetric, e.g., a slight tremor of the fingers on one hand at rest, and then become bilateral. Symptoms of Parkinson's disease are caused by loss of nerve cells in the pigmented substantia nigra pars compacta (SNPC) and the locus coeruleus in the midbrain. The stratium or corpus stratium is a structure in the cerebral hemispheres consisting of two basal ganglia (the caudate nucleus and the putnam) and the fibre of the internal capsule that separate them. Parkinson's disease in humans primarily effects the subcortical structures, especially the substantai nigra and the locus ceruleus. It is characterized by the loss of dopamine neurons in the substanta nigra, which have the basal ganglia as their major target organ. Cell loss also occurs in the globus pallidus and putamen.

Parkinson's disease is also associated with eosinophilic intraneural inclusion granules (Lewy bodies) which are present in the basal ganglia, brainstem, spinal cord, and sympathetic ganglia. The pars compacta neurons of the substantia nigra (SN) provide dopaminergic input into the stratium, which is part of the basal ganglia. These dopaminergic neurons modulate a monosynaptic gamma-aminobutyric acid (GABA) inhibitory output in the globus pallidus interna and pars reticulata of the substantia nigra. In Parkinson's disease, loss of dopaminergic cells in the substantia nigra leads to stratial dopamine depletion. This loss of dopamine alters the activity of neurons within the basal ganglia circuitry, including excessive firing and activity of these cells.

Accordingly, for the treatment of neurodegenarive disease of the substantia nigra, a vector comprising a therapeutic agent, e.g., a nucleotide sequence encoding GAD, can be delivered to the site of domaminergic cell loss or other regions of the basal ganglia and output nuclei. In one embodiment, the vector comprising a therapeutic agent can be delivered to the subthalmic nucleus (SN). In another embodiment, the vector comprising a therapeutic agent can be delivered to the substantia nigra pars reticulata (SNPR).

(b) Alzheimer's Disease

Alzheimer's disease is characterized by the gradual loss of intellectual capabilities. Post-mortem examination of the brain shows a generalized atrophy. There are extensive histologic changes in Alzheimer's disease dominated by the presence of intracellular amyloid plaques and neurofibrillary tangles. Plaques and tangles are rare, however, in the basal ganglia and substantia nigra. Many specimens from Alzheimer's disease patients demonstrate a loss of pigmentation in the area of the locus ceruleus, which is a major source of noradrenergic synthesis in the brain.

II. Gamma Aminobutyric Acid (GABA) and Glutamic Acid Decarboxylase (GAD)

Gamma aminobutyric acid (GABA) and glutamic acid are two major neurotransmitters involved in the regulation of brain neuronal activity. GABA is the major inhibitory neurotransmitter and L-glutamic acid is an excitatory transmitter (Roberts et al. GABA in Nervous System Function, Raven Press: New York, 1976; McGeer et al. Glutamine, Glutamate, and GABA in the Central Nervous System; Hertz L, Kvamme E, McGeer E G, Schousbal A, eds., Liss: New York, 1983;3-17). GABA is released from dopaminergic cells. An imbalance in the concentration of these neurotransmitters can lead to convulsive states. When the concentration of GABA diminishes below a threshold level in the brain, convulsions result (Karlsson et al., (1974) *Biochem. Pharmacol.* 23:3053-3061). When the GABA levels rise in the brain the convulsions terminate (Hayashi (1959) supra). In several convulsive disorders there is concomitant with reduced brain GABA levels a diminished level of glutamic acid decarboxylase (GAD) activity (McGeer et al., GABA in Nervous System Function; Roberts E, Chase T N, Tower D B, eds., Raven Press: New York 1976:487-495; Butterworth et al., (1983) *Neurochem.* 41:440-447). The concentrations of GAD and GABA vary in parallel because decreased GAD concentration results in lower GABA production.

GABA interacts with a least two receptors, GABA-A and GABA-B. GABA-A receptors have been well characterized and are coupled to chloride channels (Bormann (1988) *Trends Neurosci.* 11: 112-116). GABA-A receptors are related to ligand gated ion channels belonging to the same superfamily as the nicotrinic receptor for achetylcholine. In contrast, GABA-B receptors are less well understood, although reports describe that the GABA-B receptors are coupled to either calcium or potassium channels (Bormann (1988) *Trends Neurosci.* 11: 112-116 supra).

The majority of neurons in the striatum (caudate-putamen, dorsal striatum; nucleus accumbens, ventral striatum) and in striatal projection regions (the pallidum, the entopeduncular nucleus and substantia nigra reticulata) use GABA as transmitter and express GAD in the synthesis of GABA. Brain contains at least two molecular forms of GAD, the principal synthetic enzyme for GABA. Two forms, termed GAD-65 and GAD-67, are the products of two genes and differ in sequence, molecular weight, and level of expression among brain regions. GAD-65 appears to be localized in nerve terminals to a greater degree than GAD-67, which appears to be more uniformly distributed throughout the cell. Although GAD-65 and GAD-67 differ significantly in several characteristics, they also have substantial similarities and interactions, and the presence of individual forms of GAD in certain cell types is consistent with the idea that GAD-65 and GAD-67 can each synthesize GABA. Thus, GAD-65 and GAD-67 seem to provide a dual system for the control of neuronal GABA synthesis. Specific changes in activity in subpopulations of striatal GABA neurons mediate the dopamine-dependent effects seen in Parkinson's disease (Lindefors (1993) *Prog Neuropsychopharmacol Biol Psychiatry* 17:887-903).

Human GAD-65 and GAD-67 have been isolated and cloned by Bu et al. (1992) *Proc Natl Acad Sci* 89:2115-2119. Human GAD-65 cDNA encodes a Mr 65,000 polypeptide, with 585 amino acid residues (Genbank Accession No. NM000818;M81882), Human GAD-67 encodes a Mr 67,000 polypeptide, with 594 amino acid residues (Genbank Accession No. NM013445;M81883).

In one embodiment, the invention features a vector comprising a nucleotide sequence encoding GAD-65. In another embodiment, the invention features a vector comprising a nucleotide sequence encoding GAD-67.

Also within the scope of the invention is a polypeptide encoded by nucleotide sequence that has at least 60% homology to GAD-65 or a fragment thereof. A polypeptide encoded by nucleotide sequence that about 70% homology, about 75% homology, about 80% homology, about 85% homology, about 90% homology, about 95% homology, about 99% homology to GAD-65 or a fragment thereof. Also within the scope of the invention is a polypeptide encoded by nucleotide sequence that has at least 60% homology to GAD-67 or a fragment thereof. A polypeptide encoded by nucleotide sequence that about 70% homology, about 75% homology, about 80% homology, about 85% homology, about 90% homology, about 95% homology, about 99% homology to GAD-67 or a fragment thereof.

The GAD transduction in target cells of the STN will specifically increase the local inhibitory tone, acting via increasing extracellular GABA and inhibiting neuronal activity in the STN by acting on both GABA-A and GABA-B receptors. Gene expression using the method of the invention provides completely stable levels of the transgene expression for at least 15 months in vivo (see Example 3). The release of GABA from the transduced cells diffuses locally binds to the GABA receptors thereby leading to significant depression of activity. Importantly, unlike either ablation or DBS, the gene transfer using AAV is devoid of any cellular infiltration, any microglial cell activation and lack of reactive astrocytosis. Each of these compensatory or inflammatory responses to the ablative or DBS approaches is likely to reduce the efficacy of these respective strategies and potentially have other.

Other inhibitory genes that can be used in the method of the invention includes, but are not limited to, genes which encode potassium channels, genes which encode other ion channels and genes that act on the neurotransmitter release machinery, including endocytosis and exocytosis. Examples of genes include for example, frequenin and AP 180.

III. Vectors

The vectors of the invention can be delivered to the cells of the central nervous system by using viral vectors or by using non-viral vectors. In a preferred embodiment, the invention uses adeno-associated viral vectors comprising the a nucleotide sequence encoding GAD for gene delivery. AAV vectors can be constructed using known techniques to provide at least the operatively linked components of control elements including a transcriptional initiation region, a exogenous nucleic acid molecule, a transcriptional termination region and at least one post-transcriptional regulatory sequence. The control elements are selected to be functional in the targeted cell. The resulting construct which contains the operatively linked components is flanked at the 5' and 3' region with functional AAV ITR sequences.

The nucleotide sequences of AAV ITR regions are known. The ITR sequences for AAV-2 are described, for example by Kotin et al. (1994) *Human Gene Therapy* 5:793-801; Berns "Parvoviridae and their Replication" in Fundamental Virology, 2nd Edition, (B. N. Fields and D. M. Knipe, eds.) The skilled artisan will appreciate that AAV ITR's can be modified using standard molecular biology techniques. Accordingly, AAV ITRs used in the vectors of the invention need not have a wild-type nucleotide sequence, and may be altered, e.g., by the insertion, deletion or substitution of nucleotides. Additionally, AAV ITRs may be derived from any of several AAV serotypes, including but not limited to, AAV-1, AAV-2, AAV-3, AAV-4, AAV-5, AAVX7, and the like. Furthermore, 5' and 3' ITRs which flank a selected nucleotide sequence in an AAV expression vector need not necessarily be identical or derived from the same AAV serotype or isolate, so long as the ITR's function as intended, i.e., to allow for excision and replication of the bounded nucleotide sequence of interest when AAV rep gene products are present in the cell.

The skilled artisan can appreciate that regulatory sequences can often be provided from commonly used promoters derived from viruses such as, polyoma, Adenovirus 2, cytomegalovirus and Simian Virus 40. Use of viral regulatory elements to direct expression of the protein can allow for high level constitutive expression of the protein in a variety of host cells. Ubiquitously expressing promoters can also be used include, for example, the early cytomegalovirus promoter Boshart et al. (1985) *Cell* 41:521-530, herpesvirus thymidine kinase (HSV-TK) promoter (McKnight et al. (1984) *Cell* 37: 253-262), β-actin promoters (e.g., the human β-actin promoter as described by Ng et al. (1985) *Mol. Cell Biol.* 5: 2720-2732) and colony stimulating factor-1 (CSF-1) promoter (Ladner et al. (1987) *EMBO J.* 6: 2693-2698).

Alternatively, the regulatory sequences of the AAV vector can direct expression of the gene preferentially in a particular cell type, i.e., tissue-specific regulatory elements can be used. Non-limiting examples of tissue-specific promoters which can be used include, central nervous system (CNS) specific promoters such as, neuron-specific promoters (e.g., the neurofilament promoter; Byrne and Ruddle (1989) *Proc. Natl. Acad. Sci. USA* 86:5473-5477) and glial specific promoters (Morii et al. (1991) *Biochem. Biophys Res. Commun.* 175: 185-191). Preferably, the promoter is tissue specific and is essentially not active outside the central nervous system, or the activity of the promoter is higher in the central nervous system that in other systems. For example, a promoter specific for the spinal cord, brainstem, (medulla, pons, and midbrain), cerebellum, diencephalon (thalamus, hypothalamus), telencephalon (corpus stratium, cerebral cortex, or within the cortex, the occipital, temporal, parietal or frontal lobes), or combinations, thereof. The promoter may be specific for particular cell types, such as neurons or glial cells in the CNS. If it is active in glial cells, it may be specific for astrocytes, oligodentrocytes, ependymal cells, Schwann cells, or microglia. If it is active in neurons, it may be specific for particular types of neurons, e.g., motor neurons, sensory neurons, or interneurons. Preferably, the promoter is specific for cells in particular regions of the brain, for example, the cortex, stratium, nigra and hippocampus.

Suitable neuronal specific promoters include, but are not limited to, neuron specific enolase (NSE) (Olivia et al. (1991) *Genomics* 10: 157-165, GenBank Accession No: X51956), and human neurofilament light chain promoter (NEFL) (Rogaev et al. (1992) *Hum. Mol. Genet.* 1: 781, GenBank Accession No: L04147). Glial specific promoters include, but are not limited to, glial fibrillary acidic protein (GFAP) promoter (Morii et al. (1991) *Biochem. Biophys Res. Commun.* 175: 185-191, GenBank Accession No:M65210), S100 promoter (Morii et al. (1991) *Biochem. Biophys Res. Commun.* 175: 185-191, GenBank Accession No: M65210) and glutamine synthase promoter (Van den et al. (1991) *Biochem. Biophys. Acta.* 2: 249-251, GenBank Accession No: X59834). In a preferred embodiment, the gene is flanked upstream (i.e., 5') by the neuron specific enolase (NSE) promoter. In another preferred embodiment, the gene of interest is flanked upstream (i.e., 5') by the elongation factor 1 alpha (EF) promoter.

The AAV vector harboring the nucleotide sequence encoding a protein of interest, e.g., GAD, and a post-transcriptional regulatory sequence (PRE) flanked by AAV ITRs, can be constructed by directly inserting the nucleotide sequence encoding the protein of interest and the PRE into an AAV genome which has had the major AAV open reading frames ("ORFs") excised therefrom. Other portions of the AAV genome can also be deleted, as long as a sufficient portion of the ITRs remain to allow for replication and packaging functions. These constructs can be designed using techniques well known in the art. (See, e.g., Lebkowski et al. (1988) *Molec. Cell. Biol.* 8:3988-3996; Vincent et al. (1990) *Vaccines 90* (Cold Spring Harbor Laboratory Press); Carter (1992) *Current Opinion in Biotechnology* 3:533-539; Muzyczka (1992) *Current Topics in Microbiol. and Immunol.* 158:97-129; Kotin (1994) *Human Gene Therapy* 5:793-801; Shelling et al. (1994) *Gene Therapy* 1:165-169; and Zhou et al. (1994) *J. Exp. Med.* 179:1867-1875).

Alternatively, AAV ITRs can be excised from the viral genome or from an AAV vector containing the same and fused 5' and 3' of a selected nucleic acid construct that is present in another vector using standard ligation techniques, such as those described in Sambrook et al., Supra. Several AAV vectors are available from the American Type Culture Collection ("ATCC") under Accession Numbers 53222, 53223, 53224, 53225 and 53226.

In order to produce recombinant AAV particles, an AAV vector can be introduced into a suitable host cell using known techniques, such as by transfection. A number of transfection techniques are generally known in the art. See, e.g., Graham et al. (1973) *Virology,* 52:456, Sambrook et al. (1989) Molecular Cloning, a laboratory manual, Cold Spring Harbor Laboratories, N.Y., Davis et al (1986) Basic Methods in Molecular Biology, Elsevier, and Chu et al. (1981) *Gene* 13:197. Particularly suitable transfection methods include calcium phosphate co-precipitation (Graham et al. (1973) *Virol.* 52:456-467), direct micro-injection into cultured cells (Capecchi (1980) *Cell* 22:479-488), electroporation (Shigekawa et al. (1988) *BioTechniques* 6:742-751), liposome mediated gene transfer (Mannino et al. (1988) *BioTechniques* 6:682-690), lipid-mediated transduction (Felgner et al. (1987) *Proc. Natl. Acad. Sci. USA* 84:7413-7417), and nucleic acid delivery using high-velocity microprojectiles (Klein et al. (1987) *Nature* 327:70-73).

Suitable host cells for producing recombinant AAV particles include, but are not limited to, microorganisms, yeast cells, insect cells, and mammalian cells, that can be, or have been, used as recipients of a exogenous nucleic acid molecule. Thus, a "host cell" as used herein generally refers to a cell which has been transfected with an exogenous nucleic acid molecule. The host cell includes any eukaryotic cell or cell line so long as the cell or cell line is not incompatible with the protein to be expressed, the selection system chosen or the fermentation system employed. Non-limiting examples include CHO dhfr– cells (Urlaub and Chasin (1980) *Proc. Natl. Acad. Sci. USA* 77:4216-4220), 293 cells (Graham et al. (1977) *J. Gen. Virol.* 36: 59) or myeloma cells like SP2 or NS0 (Galfre and Milstein (1981) *Meth. Enzymol.* 73(B):3-46).

In one embodiment, cells from the stable human cell line, 293 (readily available through, e.g., the ATCC under Accession No. ATCC CRL1573) are preferred in the practice of the present invention. Particularly, the human cell line 293, which is a human embryonic kidney cell line that has been transformed with adenovirus type-5 DNA fragments (Graham et al. (1977) *J. Gen. Virol.* 36:59), and expresses the adenoviral E1a and E1b genes (Aiello et al. (1979) *Virology* 94:460). The 293 cell line is readily transfected, and provides a particularly convenient platform in which to produce rAAV virions.

Host cells containing the above-described AAV vectors must be rendered capable of providing AAV helper functions in order to replicate and encapsidate the expression cassette flanked by the AAV ITRs to produce recombinant AAV particles. AAV helper functions are generally AAV-derived coding sequences which can be expressed to provide AAV gene products that, in turn, function in trans for productive AAV replication. AAV helper functions are used herein to complement necessary AAV functions that are missing from the AAV vectors. Thus, AAV helper functions include one, or both of the major AAV open reading frames (ORFs), namely the rep and cap coding regions, or functional homologues thereof.

The AAV rep coding region of the AAV genome encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other exogenous) promoters. The Rep expression products are collectively required for replicating the AAV genome. The AAV cap coding region of the AAV genome encodes the capsid proteins VP1, VP2, and VP3, or functional homologues thereof.

AAV helper functions can be introduced into the host cell by transfecting the host cell with an AAV helper construct either prior to, or concurrently with, the transfection of the AAV vector comprising the expression cassette, AAV helper constructs are thus used to provide at least transient expression of AAV rep and/or cap genes to complement missing AAV functions that are necessary for productive AAV infection. AAV helper constructs lack AAV ITRs and can neither replicate nor package themselves. These constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. (See, e.g., Samulski et al. (1989) *J. Virol.* 63:3822-3828; and McCarty et al. (1991) *J. Virol.* 65:2936-2945). A number of other vectors have been described which encode Rep and/or Cap expression products. See, e.g., U.S. Pat. No. 5,139,941.

As a consequence of the infection of the host cell with a helper virus, the AAV Rep and/or Cap proteins are produced. The Rep proteins also serve to duplicate the AAV genome. The expressed Cap proteins assemble into capsids, and the AAV genome is packaged into the capsids. This results the AAV being packaged into recombinant AAV particles comprising the expression cassette. Following recombinant AAV replication, recombinant AAV particles can be purified from the host cell using a variety of conventional purification methods, such as CsCl gradients. The resulting recombinant AAV particles are then ready for use for gene delivery to various cell types.

Alternatively, a vector of the invention can be a virus other than the adeno-associated virus, or portion thereof, which allows for expression of a nucleic acid molecule introduced into the viral nucleic acid. For example, replication defective retroviruses, adenoviruses and lentivirus can be used. Protocols for producing recombinant retroviruses and for infecting cells in vitro or in vivo with such viruses can be found in Current Protocols in Molecular Biology, Ausubel et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines include Crip, Cre, 2 and Am. The genome of adenovirus can be manipulated such that it encodes and expresses the protein of interest but is inactivated in terms of its ability to replicate in a normal lytic viral life cycle. See e.g., Berkner et al. (1988) *BioTechniques* 6:616; Rosenfeld et al. (1991) *Science* 252:431-434; and Rosenfeld et al. (1992) *Cell* 68:143-155. Suitable adenoviral vectors derived from the adenovirus strain Ad type 5 dl324 or other strains of adenovirus (e.g., Ad2, Ad3, Ad7 etc.) are well known to those skilled in the art.

Alternatively, the vector can be delivered using a non-viral delivery system. This includes delivery of the vector to the desired tissues in colloidal dispersion systems that include, for example, macromolecule complexes, nanocapsules, microspheres, beads, and lipid-based systems including oil-in-water emulsions, micelles, mixed micelles, and liposomes. Liposomes are artificial membrane vesicles which are useful as delivery vehicles in vitro and in vivo. In order for a liposome to be an efficient gene transfer vehicle, the following characteristics should be present: (1) encapsulation of the genetic material at high efficiency while not compromising the biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al. (1988) *Biotechniques*, 6:682). Examples of suitable lipids liposomes production include phosphatidyl compounds, such as phosphatidylglycerol, phosphatidylcholine, phosphatidylserine, phosphatidylethanolamine, sphingolipids, cerebrosides, and gangliosides. Additional examples of lipids include, but are not limited to, polylysine, protamine, sulfate and 3b-[N-(N', N' dimethylaminoethane) carbamoyl] cholesterol.

Alternatively, the vector can be coupled with a carrier for delivery Exemplary and preferred carriers are keyhole limpet hemocyanin (KLH) and human serum albumin. Other carriers may include a variety of lymphokines and adjuvants such as INF, IL-2, IL-4, IL-8 and others. Means for conjugating a peptide to a carrier protein are well known in the art and include glutaraldehyde, m-maleimidobenzoyl-N-hydroxysuccinimide ester, carbodiimyde and bis-biazotized benzidine. The vector can be conjugated to a carrier by genetic engineering techniques that are well known in the art. (See e.g., U.S. Pat. Nos. 4,608,251; 4,601,903; 4,599,231; 4,599,230; 4,596,792; and 4,578,770).

In one embodiment, particle-mediated delivery using a gene-gun can be used as a method to deliver the vector. Suitable particles for gene gun-based delivery of include gold particles. In one embodiment, the vector can be delivered as naked DNA. Gene gun based delivery is described, for example by, Braun et al. (1999) *Virology* 265:46-56; Drew et al. (1999) *Vaccine* 18:692-702; Degano et al. (1999) *Vaccine* 18:623-632; and Robinson (1999) *Int J Mol Med* 4:549-555; Lai et al. (1998) *Crit Rev Immunol* 18:449-84; See e.g., Accede et al. (1991) *Nature* 332: 815-818; and Wolff et al. (1990) *Science* 247:1465-1468 Murashatsu et al., (1998) *Int. J. Mol. Med.* 1: 55-62; Agracetus et al. (1996) *J. Biotechnol.* 26: 37-42; Johnson et al. (1993) *Genet. Eng.* 15: 225-236). Also within the scope of the invention is the delivery of the vector in one or more combinations of the above delivery methods.

IV. Delivery Systems

Delivery systems include methods of in vitro, in vivo and ex vivo delivery of the vector. For in vivo delivery, the vector can be administered to a subject in a pharmaceutically acceptable carrier. The term "pharmaceutically acceptable carrier", as used herein, refers to any physiologically acceptable carrier for in vivo administration of the vectors of the present invention. Such carriers do not induce an immune response harmful to the individual receiving the composition, and are discussed in section V. In one embodiment, vector can be distributed throughout a wide region of the CNS, by injecting the vector into the cerebrospinal fluid, e.g., by lumbar puncture (See e.g., Kapadia et al. (1996) *Neurosurg* 10: 585-587).

Alternatively, precise delivery of the vector into specific sites of the brain, can be conducted using stereotactic microinjection techniques. For example, the subject being treated can be placed within a stereotactic frame base (MRI-compatible) and then imaged using high resolution MRI to determine the three-dimensional positioning of the particular region to be treated. The MRI images can then be transferred to a computer having the appropriate stereotactic software, and a number of images are used to determine a target site and trajectory for antibody microinjection. The software translates the trajectory into three-dimensional coordinates that are precisely registered for the stereotactic frame. In the case of intracranial delivery, the skull will be exposed, burr holes will be drilled above the entry site, and the stereotactic apparatus used to position the needle and ensure implantation at a predetermined depth. The vector can be delivered to regions, such as the cells of the spinal cord, brainstem, (medulla, pons, and midbrain), cerebellum, diencephalon (thalamus, hypothalamus), telencephalon (corpus stratium, cerebral cortex, or within the cortex, the occipital, temporal, parietal or frontal lobes), or combinations, thereof. In another preferred embodiment, the vector is delivered using other delivery methods suitable for localized delivery, such as localized permeation of the blood-brain barrier. Particularly preferred delivery methods are those that deliver the vector to regions of the brain that require modification.

Modification as used herein refers to a change in the cellular activity in the region of the brain injected with the vector. The change in cellular activity can result from changing the expression, or production of genes responsible for stimulating a cell. For example, delivery of a vector comprising a nucleotide sequence encoding GAD, to a region of the brain that is overstimulated, such as the basal ganglia. In particular, delivery of the vector to the STN which are overactive in diseases such as Parkinson's, will result in expression of GAD in this region. While not being required to provide a mechanism of action, the expression of GAD in the STN results in production of GABA within the STN cells, the STN cells release GABA locally such that the released GABA binds to GABA-A and GABA-B receptors on the STN cell surface. GABA binding to the GABA receptors results in a reduction in cell stimulation, thereby reducing overactivity in the STN cells and prevent neuronal destruction.

V. Pharmaceutical Compositions and Pharmaceutical Administration

The vector of the invention can be incorporated into pharmaceutical compositions suitable for administration to a subject. Typically, the pharmaceutical composition comprises the vector of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans. The preferred mode of administration is parenteral (e.g., intravenous, subcutaneous, intraperitoneal, intramuscular). In one embodiment, the vector is administered by intravenous infusion or injection. In another embodiment, the vector is administered by intramuscular or subcutaneous injection. In another embodiment, the vector is administered perorally. In the most preferred embodiment, the vector is delivered to a specific location using stereostatic delivery.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antigen, antibody or antibody portion) in the required amount in an appropriate solvent with one or a combination of ingredients enumerated above, as required, followed by filtered sterilization.

Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The vector of the present invention can be administered by a variety of methods known in the art. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978. The pharmaceutical compositions of the invention may include a "therapeutically effective amount" or a "prophylactically effective amount" of the vectors of the invention. A "therapeutically effective amount" refers to an amount effective, at dosages and for periods of time necessary, to achieve the desired therapeutic result. A therapeutically effective amount of the vector may vary according to factors such as the disease state, age, sex, and weight of the individual, and the ability of the vector to elicit a desired response in the individual. A therapeutically effective amount is also one in which any toxic or detrimental effects of the vector are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

EXAMPLES

Example 1

Methods and Materials (i) Vector Construction

This example describes the construction of an adeno-associated virus vector with an GAD cDNA. A full length human GAD-65 cDNA was subcloned into an AAV plasmid under the control of a 1.8 kb rat NSE (neuron specific enolase) promoter (Foress-petter et al. (1986) *J. Neurosci. Res.* 16, 141-156 (1998)) 5' of the GAD cDNA followed by the Woodchuck Hepatitis Post-Transcriptional Regulatory Element (WPRE) and a bovine growth hormone (BGH) polyadenylation site between the AAV inverted terminal repeats, as previously described (During et al. (1998) *Nature Med.* 4:1131-1135). The resulting plasmid is referred to as pAAV-NSE-GAD-WPRE.

The plasmids were packaged to generate high titer rAAV-GAD viral particles using an optimized protocol based on the original helper-free transient transfection method described by Samulski et al. (1989) *J. Virol.* 63:3822-3828), but modified by using an improved 4rd generation helper plasmid, pDG as described by Grimm et al. (1999) *Hum Gene Ther* 10, 2445-2450. The helper plasmid contains both the rep and cap open reading frames, as well the minimal set of adenoviral genes necessary for helper functions. The vectors were generated using calcium phosphate transfection of both plasmids into 293 cells. Vector stocks were purified using ammonium sulfate followed by double cesium banding. The bands containing the viral particle were isolated from the cesium chloride preparation and dialysis into suitable buffer.

Particle titers were determined using an ELISA assay kit available from (Progen, Inc.) which uses an A20 monoclonal antibody that recognizes intact particles. Purification of the viral particles was performed as described by Clark et al., (1999) *Hum. Gene. Ther.* 10: 1031-1039 and Zolutkhin et al. (1999) *Gene Therapy* 9: 973-985.

(ii) Packaging Protocol

To package the recombinant vectors, human embryonic kidney cells, 293 cells (from American Type Culture Collection (ATCC # CRL-1573)), passage 4-12 were used. The 293 kidney cells ($1.5 \times 10^7$ cells) were seeded into forty 15 cm dishes in complete DMEM (Gibco) containing 10% fetal bovine serum (Hyclone), 0.1 mM MEM non-essential amino acids solution (Gibco), 1 mM MEM sodium pyruvate (Gibco), 0.05% Penicillin-Streptomycin (5, 000 units/ml, Gibco), and incubated overnight at 37° C. When the cells were 70% confluent and 2-3 hours prior to transfection, the cells were fed fresh Iscove modified Dulbecco medium (IMDM, Gibco) containing 10% fetal bovine serum (Hyclone) without antibiotics.

All plasmids were isolated from the cells by the alkaline lysis method (Sambrook et al., supra), and were further purified by HPLC (BioCAD, Sprint, PerSeptive Biosystems), and concentrated with 2 volumes of 100% ethanol (AR grade, BDH). All HPLC elute buffers (Buffer A: 250 mM Tris HCl, 10 mM EDTA, pH 8.0; Buffer B: 25 mM Tris HCl, 1 mM EDTA, 2M NaCl, pH, 8.0; Buffer C: Milli Q water) used for purification were autoclaved and filter sterilized prior to use. For each 15 cm tissue culture plate, a total of 60 μg of plasmid DNA was dissolved in 3.0 ml of 0.25M $CaCl_2$ and then quickly mixed with 3.0 ml of HEPES-buffered saline (50 mM HEPES, 280 mM NaCl, 1.5 mM $Na_2HPO_4$ [pH 7.05-7.10]), incubated for 2 min and then added to the cells. 6-8 hours after transfection, the medium was aspirated and cells were washed with IMDM supplemented with 10% fetal bovine serum without antibiotics. The washing medium was then aspirated and replaced with fresh IMDM (Gibco) containing 10% fetal bovine serum with trace pen/strep. The cells were harvested at 48 hours after transfection. After low-speed centrifugation on a tabletop centrifuge, the cell pellets were resuspended in 20 ml of Opti-MEM (Gibco) and subjected to sonication using 15-20% energy for 50 bursts lasting 1 min. Cell debris was removed with low speed centrifugation. The clarified supernatant was collected into a 50 ml polypropylene tube, the cell pellets were resuspended in 20 ml of Opti-MEM for reextraction. The supernatants were combined.

One-third volume of ice-cold saturated $(NH_4)_2SO_4$ was added to the supernatant, mixed and placed on ice for 10 minutes. The sample was then centrifuged at 8,000 rpm at 4° C. for 10 min, supernatant was transferred to a polypropylene centrifuge tube, ⅔ volume of the initial lysate of saturated $(NH_4)_2SO_4$ was added and mixed well, then placed on ice for 20 min prior to centrifugation at 12,000 rpm for 20 min at 4° C. The pellet was redissolved in CsCl-phosphate-buffered saline (PBS) (pH 7.4) solution (density 1.37 g/l) and centrifuged in an SW41 rotor Beckman at 80,000 rpm (for 24 hours with a 0.5 ml CsCl-PBS cushion (density, 1.5 g/ml).

The band containing recombinant AAV particle (rAAV) was collected and re-centrifuged as described above for a further 24 hours. Finally, the rAAV band was collected following the second CsCl centrifugation and dialyzed against one liter sterile dialysis buffer containing 50 mM NaCl, 5 mM Tris-HCl and 0.5 mM $MgCl_2$ (pH 7.4) for an initial 4 hours. Dialysis was repeated using one liter of fresh cold sterile dialysis buffer for another 4 hours and finally overnight dialysis using a 50,000 molecular weight cut off dialysis membrane (Spectrapor) and fresh sterile dialysis buffer. The AAV virus particle titer was determined using an ELISA method described by Wistuba et al. ((1997) *J. Virol.* 71: 1341-1352). Briefly, a monoclonal antibody specific for AAV assembled capsids is coated onto microtiter strips and is used to capture AAV particles. A biotin-conjugated monoclonal antibody to AAV is bound to the immune complex, streptavidin peroxidase conjugate reacts with the biotin molecules. Addition of substrate solution results in a color reaction which is proportional to specifically bound virus particles, and allows the quantitative determination of an unknown particle titer.

Viral particle titre was also determined by the AAV titration ELISA kit is provided by Progen (Germany). One hundred microliter of ready-to-use wash buffer, positive, negative controls, and dilutions of standard and samples were pipetted into appropriate wells of the microtiter strips which were sealed with adhesion foil. After incubation for 1 hour at 37° C., the solution was removed and each well was rinsed 3 times with 200 µl of washing buffer for 30 seconds. The washing buffer was removed and 100 µl of ready to use biotin conjugate was added. The strips were sealed with adhesion foil and incubated for one hour at 37° C. The strips were washed as described above. A volume of 100 µl of ready-to-use streptavidin conjugate was added, and the strips were sealed with adhesion foil and incubated for one hour at 37° C. The washing steps were then repeated as described above. Substrate at a volume of 100 µl was pipetted into each well and incubated at room temperature for 10 min. The reaction was stopped by adding 100 µl of stop solution into each well. Absorbance of each well was measured photometrically at 450 nm wavelength.

(iii) Determination of AAV Particle to Transducing Unit Ratio.

To determine the transducing unit ratio of the AAV particles, 293 cells were seeded onto a collagen-coated 24 well plate at a cell number of $5 \times 10^4$ cells/well. The cells were grown in Dulbecco's modified Eagle medium (DMEM, GIBCO) containing 10% fetal bovine serum (Hyclone), 0.1 mM MEM non-essential amino acids solution (GIBCO), 1 mM MEM sodium pyruvate (GIBCO), 0.05% Penicillin-Streptomycin (5,000 units/ml, GIBCO), at 5% $CO_2$, 37° C. overnight. AAV/gfap-TH virus at a volume of 0.5 ml was added to each well and incubated for 48 hours.

For rat primary neurons and glia, E15 rats was used for nigra and cortex preparation, while E18 rats were used for hippocampal and striatal primary cell preparation. The primary cultures were pipetted into poly-1-lysine-treated 24 well plates at 250,000 cells per well, and incubated in 5% $CO_2$, at 37° C. for 24-48 hours. Following the incubation, medium B containing 15% FCS, 0.6% glucose, 100 U/100 µg per ml pen/strep in DMEM/F12 was added to the cultures and the cultures incubated. After 3 days incubation, 0.5 ml of AAV virus was added onto the cortical culture. After 4-5 days incubation, 0.5 ml of AAV/gfpa-TH virus was added onto nigral, hippocampual and striatal cultures. All medium was replaced with fresh culture medium one day before the virus addition, cultures were incubated in 5% $CO_2$, at 37° C. for 3 days. The cells were then fixed with 4% paraformaldehyde in 0.1 M phosphate buffer (pH 7.4) for 15 min, and washed with phosphate buffered saline (PBS) containing Triton x100. TH antibody (dilution 1:500, Boehringer Mannheim) was used to determine total TH level, while haemogglutin (HA) antibody (dilution 1:500, Berkeley Antibody Company) was used to confirm exogenous TH immunoreactivity. The numbers of positive cells was counted.

Example 2

In vitro Transduction of the AAVGAD Vectors

The GAD-65 and GAD-67 vectors were transduced into primary neuronal cultures from the subthalamic nucleus. FIG. 1 shows an image of cells infected with AAV vectors expressing GAD-67 (top two panels) with a MOI of 10 (multiplicity of infection) in transient transfection experiments. The antibodies were detected using a commercially available antibody for Immunocytochemical detection. A similar experiment was conducted using cells infected with AAV vectors expressing GAD-65 with an MOI of 10 (middle two panels), and detected using an antibody specific for GAD-65. This data demonstrates successful transduction of vectors and successful expression of the vectors in-vitro in primary neuronal cultures from the subthalamic nucleus.

Example 3

Additional Vector Constructs and Materials

Other AAV plasmid constructs that can be used include those containing different enhancers and promoters. For example, an AAV plasmid construct for GAD65 with a 1.1 kb Cytomegalovirus Enhancer/Chicken-Actin (CBA) hybrid promoter, 1760 base pair (bp) human GAD65 cDNA (Genbank accession number M81882), 647 bp Woodchuck Hepadnavirus Post Transcriptional Regulatory Element (WPRE), 269 bp Bovine Growth Hormone Polyadenylation sequence (BGH-polyA), flanked by 145 bp AAV Inverted Terminal Repeats (ITRs). This construct is referred to as pAM/CBA-hGAD65-WPRE-BGHpolyA.

Another AAV plasmid construct for GAD67 is one with a 1.1 kb CBA promoter, 1780 bp human GAD67 cDNA (Genbank accession number M81883), 647 bp WPRE, 269 bp BGH-polyA, flanked by 145 bp AAV ITRs. This construct is referred to as pAM/CBA-hGAD67-WPRE-BGHpolyA.

The advantages using CBA is demonstrated by Xu et al., have shown that an AAV vector with the CBA promoter resulted in 9.5-fold higher expression after portal vein injection compared with an AAV vector with the EFlalpha promoter, and 137-fold higher expression than an AAV vector with the CMV promoter/enhancer (Xu et al. (2001) *Hum Gene Ther.* 12:563-73).

The constructs also contains a 647 bp Woodchuck hepadnavirus postregulatory element (WPRE), originating from the 3' region of the viral S transcript, directly downstream of the human GAD genes. WPRE appears to be important for high-level expression of native mRNA transcripts, acting to enhance mRNA processing and transport of intronless genes (Donello et al. (1998) *J. Virol.* 72: 5085-92).

The bovine growth hormone polyadenylation (BGH-polyA) sequence used in the constructs, drives higher expression than other polyA sequences such as SV40 early polyA and human collagen polyA, and was thus incorporated to enhance expression (Pfarr et al. (1986) *DNA* 5:115-22).

(i) Construction of pAM/CB-hGAD65-WPRE-BGH and pAM/CB-hGAD67-WPRE-BGH

The DNA cassette that was packaged inside each AAV virion contains the AAV Inverted Terminal Repeats derived from pSub201 (pSub201) is also known as pSSV9. pSub201 was first described in the *J. Virol.* (1987)61:3096-3101 by R. Samulski and coworkers. This vector contains all of the Adeno-Associated Virus type 2 (AAV-2) wild-type coding regions and cis-acting terminal repeats cloned into a plasmid backbone. This vector is ideal for cloning, and was engineered in such a way that restriction digest with Xba I allowed the removal of the AAV coding region while leaving the AAV terminal repeats intact in the plasmid backbone. This is important because the terminal repeats are the only cis acting sequences required for recombinant virus production.

The unpackaged backbone of the AAV plasmid (pAM) was derived from plasmid pSV2-gpt (ATCC 37145). The insert containing the ampicillin resistance gene, the *E coli.* ori and the SV40 ori was cloned out of pSV2-gpt using the EcoRI and HindIII sites. The pSub201 backbone was swapped for the pSV2-gpt insert leaving the AAV ITRs. The SV40 ori was inserted adjacent to the 5' ITR. WPRE-BGH was inserted into SacI and SalI which created pAM-pL-WPRE-BGH. Next, the rat Neuron Specific Enolase (NSE) promoter (Peel, Zolotukhin et al. 1997), acting as an intermediate promoter, was inserted into the rAAV/pL-WPRE-BGH at the 5' ITR using Asp718 and HindIII. This NSE-polylinker-WPRE-BGH cloning plasmid provided the basis for cloning CBA-GAD65-WPRE and CBA-GAD67-WPRE.

(ii) PCR to Obtain GAD65 and GAD67 PCR Amplification and Subcloning of AAV/CBA-hGAD65-WPRE pBluescript II SK+ plasmids containing human GAD65 and GAD67 cDNAs were used. Firstly, the ATG start codon and, 5' and 3' flanking sequences were removed by PCR amplification, using the following primers;

```
                                        (SEQ ID NO: 1)
hGAD65up (5' ATATATCTCGAGATGGCATCTCGGGGCTC 3')
and (SEQ ID NO: 2)
hGAD65lo (5' GCGCGCGAATTCTTATAAATCTTGTCCAAGGCG 3').
```

The PCR product was amplified using Expand Polymerase (Roche Molecular Biochemicals) with the following cycling parameters: Cycle 1: 94° C. 5 min; Cycles 2-4: 94° C. 30 sec, 50° C. 30 sec, 72° C. 2 min, Cycles 5-24: 94° C. 30 sec, 72° C. 2 min, Cycle 25: 72° C. 5 min. The 1.76 kb product was digested with EcoRI and XhoI and subcloned into EcoRI and XhoI digested pBSII KS+ as an intermediate cloning step.

The 1.76 kb hGAD65 insert was removed from pBSII Sk+ with XhoI (blunt) and EcoRI and inserted into NotI (blunt) and EcoRI of pAM/NSE-pl-WPRE-bGH to create pAM/NSE-hGAD65-WPRE bGH.

The CMV enhancer/chicken B-actin (CBA) hybrid promoter was removed from pBACMAM3 (Novagen) with HgaI (blunt/partial) and EcoRI (blunt) and inserted into Asp718 (blunt) and EcoRI (blunt) digested pAM/NSE-hGAD65-WPRE to create pAM/CBA-hGAD65-WPRE.

(iii) PCR Amplification and Subcloning of AAV/CBA-hGAD67-WPRE

The corresponding plasmid containing hGAD67 (1.78 kb) was constructed by PCR amplification of hGAD67 from pBSII SK+/hGAD67 (2.01 kb).

The following primers were used:

```
                                          (SEQ ID NO: 3)
hGAD67up   (5' TATATCTCGAGATGGCGTCTTCGACCCA 3')
and (SEQ ID NO: 4)
hGAD67lo   (5' CAGCTGAATTCTTACAGATCCTGGCCCAG 3').
```

The PCR conditions used were identical to those used for hGAD65 amplification (See above). The 1.78 kb PCR product was digested with XhoI and EcoRI and inserted into XhoI and EcoRI digested pBSII KS+ as an intermediate cloning site. hGAD67 was removed from pBSII KS+/hGAD67 with XhoI (blunt) and EcoRI and inserted into BamHI (blunt) and EcoRI of pAM/CBA-hGAD65-WPRE to create pAM/CBA-hGAD67-WPRE.

iv Protocal for Vector Production and Punfication Cell Growth

The 293 cells were cultured in conditions to optimize transfection. (Confluency and Media detailed in SOP.

Transfection

Calcium chloride was used in conjunction with the AAV plasmid (containing GAD65 or 67) and the packaging/helper plasmids (pRV1 and PFΔ6) to transfect 293 cells with both plasmids. A Media wash was then performed.

Harvesting Cells

Cells were washed in PBS, then sodium deoxycholate and benzonase was added. Sodium deoxycholate is used to lyse the cell membranes, and benzonase is an endonucleaused to breat up cellular DNA and RNA. The mixture was centrifuged to pellet cellular components/debris, with the rAAV fraction being left in the supernatant.

Heparin Column Purification

A heparin column was used to purify rAAV, based on heparin being a ligand for rAAV. The eluted rAAV was then concentrated by centrifugation and twice dialyzed. The dialyzed rAAV was then further purified by filtration, and finally aliquoted.

Quality Control rAAV taken from above was run on a protein gel and stained with coomassie brilliant blue to assess purity. A Western blot is run with anti VP1, 2 & 3 to verify the presence of the viral capsid proteins (identity testing).

(v) Genomic Titer Assay for rAAV

Genomic titering was performed using the Perkin Elmer 7700 Quantitative PCR Method. This method allows quantification of genomic copy number. Two samples of the vector stock were diluted in PCR buffer (1:50 dilution, usually produces a genomic titer of $10^9$/ml), one was then used as a no DNase control. Next 350 units of DNase I (Boehringer Mannheim) were added to one sample and incubated at 37° C. for 30 mins. Following DNase treatment 10 μg of Proteinase K was added to both samples and they were incubated at 50° C. for 1 hour. Proteinase K was then inactivated by heating to 95° C. for 20 mins. A dilution series was then made for both samples. A dilution series of the rAAV plasmid containing the GAD isoform was then made with the consideration that linear amplification was possible in the range of $10^7$-$10^{12}$ total copies per ml. Both plasmid and sample dilutions were further diluted 1:4, and 5 μl of each added to a separate PCR reaction tube. A SYBR green probe was then prepared with the PCR reaction. Triplicates of each sample, standard and no template control were prepared, with a total volume for each reaction of 25 μl. The ABI Prism 7700 was used to detect the PCR reaction and incorporation of the SYBR probe in the PCR product at each cycle. A standard curve was produced by taking the average for each point in the linear range of the standard plasmid dilution series and plotting the log copy number against the average CT value for each point. An adjustment was made to take into account the single stranded genome of the rAAV as compared to the double stranded plasmid. Every 10-fold difference in copy number should correspond to approximately 3 cycles of PCR. See paper by Clark et al., (1999) Human Gene Therapy 10: 1031-39 for further details. A standardized genomic titer (dose) of $1 \times 10^{10}$ genomes per ml is sufficient to use in a patient. Stocks can be diluted to the final formulation in 1×PBS.

(vi) Infectious Titer Assay for rAAV

The infectious titer is an indicator of the concentration of rAAV particles that have the ability to enter a cell and to release their DNA cassette into the cellular milieu. This method provides reliable infectious titers for different rAAV's, independent of the particular transgene in the rAAV. Replication requires the presence of a helper virus as well as wild-type AAV genes involved in virion construction and packaging. Therefore a permissive cell line (C12) containing the rep and cap genes from the wild-type AAV genome was used in combination with coinfection using Adenovirus 5 enabling the replicative production of rAAVs when rAAV was added. Quantitative PCR was used to assess the quantity of rAAV genomes after addition to C12 cells. A dilution gradient was produced from the rAAV. Aliquots of rAAV at decreasing concentrations were added to C12 cells previously transfected with Adenovirus 5. After allowing time for replication, quantitative PCR was used to assess the number of rAAV genomes produced at each dilution of rAAV added to cells. Two controls were used in this assay. The first set of controls for the PCR amplification of the original rAAVs that were added to the cells. Aliquots from the rAAV dilution gradient were added to C12 cells without Adenovirus. No rAAV replication occurs without the presence of a helper virus. The quantitative PCR technique is sensitive enough to amplify a PCR product from the rAAV genomes originally added to the cells, but over four PCR amplification cycles were necessary to produce the same amount of the rAAV amplicon as would be present had replication occurred. The lowest dilution at which the threshold amplification was reached at least 4 cycles earlier in the cells that had both rAAV and Adenovirus added is used to calculate the infectious titer. The second control is the negative control using C12 cells without addition of either rAAV or Adenovirus. Only stocks with an infectious titer greater that $1 \times 10^9$ infectious particles per ml will be used (lot release specification).

(vii) Derivation of the Packaging/Helper Plasmid pRV1

The pRV1 plasmid was developed based on two AAV helper plasmids, pCLR1-1.5k and pCLV1, with an intron inserted into the Rep coding region and VP1 coding region, respectively (Cao et al. (2000) *J. Virol.* 74:11456-63). The 850 bp human β-globin intron 2 was amplified by PCR from human genomic DNA using primers:

```
INS1  (5' Gtt ttg gga cgt ttc ctg agt  (SEQ ID NO: 5)
      cag gtg agt cta tgg gac cct tga
      tg 3')
and INA2  (5' cag ttt ttc gcg aat ctg tgg  (SEQ ID NO: 6)
      gag gaa gat aag agg tat g 3').
```

An AAV fragment was amplified with primers:

```
VS1   (5' ccg tgg ccg aga agc tgc agc  (SEQ ID NO: 7)
      gcg act ttc 3')
and INA1  (5' cat caa ggg tcc cat aga ctc  (SEQ ID NO: 8)
      acc tga ctc agg aaa cgt ccc aaa
      ac 3').
```

The intron fragment and AAV fragment were linked together by PCR amplification using primer VS1 and INA2. The resulting fragment was digested with SfiI and NruI and cloned into pSub201 at the same sites to obtain piAAV. The resulting plasmid, piAAV has the β-globin intron at position 654. The helper plasmid pCLR1 was cloned by inserting the SfiI-NruI of piAAV850 into pAd/AAV (Samulski, et al. (1989) *J. Virol.* 63:3822-8). The 1.5 kb Lambda DNA fragments (EcoRI/HindIII digestion) was cloned into the MfeI site in the globin intron in pCLR1 to generate pCLR1-1.5k.

Plasmid pCLV1 was constructed by a similar method. The human β globin intron 2 was amplified by using primers:

```
D2    (5' cca cca cca cca aag ccc gca  (SEQ ID NO: 9)
      ggt gag tct atg gga ccc ttg at
      3')
and
```

```
D4    (5' cct gct gtc gtc ctt atg ccg  (SEQ ID NO: 10)
      ctc tgt ggg agg aag ata aga ggt
      3').
```

An AAV fragment was amplified from pAAV/Ad with primers:

```
XF    (5' agt ctc tag agt cct gta tta  (SEQ ID NO: 11)
      gag gtc acg 3')
and D2    (5' atc aag ggt ccc ata gac tca  (SEQ ID NO: 12)
      cct gcg ggc ttt ggt ggt ggt gg
      3').
```

Another AAV fragment was amplified with primers:

```
D3    (5' acc tct tat ctt cct ccc aca  (SEQ ID NO: 13)
      gag cgg cat aag gac gac agc agg
      3')
and XR    (5' cgg gtg acg tag tag tct aga  (SEQ ID NO: 14)
      gca tgg aaa 3').
```

The intron fragment and 2 AAV fragments were linked together by PCR amplification using primer XF and XR. The resulting fragment was digested with XbaI and cloned into pAAV/Ad at the same site to obtain pCLV1. The resulting plasmid pCLV1 has the β-globin intron at position 2309. These insertion sites in pCLR1-1.5k and pCLV1 correspond to the position in RNA for Rep78/68 and VP1, respectively. All these insertions in the helper plasmids maintained the consensus sequences for the splice donor sites and acceptor sites. The pRV1 plasmid was constructed by replacing the XhoI fragment in pCLR1-1.5k with the correspondent XhoI fragment containing globin intron in VP1 from pCLV1. The pRV1 plasmid has an intron inserted at position 654 and the other at 2309.

viii Derivation of Packaging/Helper Plasmid pF6

The pF6 helper plasmid was constructed from the pBHG10 plasmid. The pBHG10 plasmid was purchased from Microbix (Canada). The plasmid padF1 was constructed by cloning the Asp700/Sal I fragment with a Pme I-Sgf I deletion, isolated from pBHG10, into pBluescript. Further deletions of a 2.3 kb Nru I fragment and 0.5 kb RsrII/NruI fragment generated helper plasmid pF6.

viiii Packaging the Virions

Human embryonic 293 kidney cells were used for packaging. 293 cells were obtained from the American Type Culture Collection (ATCC # CRL-1573), and express the transforming gene of adenovirus 5 (E1 gene). The 293 cell line is a permanent line of primary human embryonal kidney transformed by sheared human adenovirus type 5 (Ad 5) DNA. The Master Cell Bank was created using cells supplied by the American Type Culture Collection (ATCC # CRL-1573). Wild-type AAV is a dependovirus which means it requires the presence of a helper virus for normal replication. In addition to the AAV helper plasmids pRV1 and pF6, the 293 cells supply the remaining helper virus sequence necessary for AAV capsid production and genome packaging.

x Transduction of Neurons

Target cells are the intrinsic neurons of the subthalamic nucleus (STN). The vector was administered at a dose of $3.5 \times 10^9$ virions in a volume of 35 microliters (based on genomic titer of rAAV stocks of $10^{11}$/ml) with an additional 15 µl of USP 25% mannitol as a flush. Based on the extensive analysis of vector distribution using AAV in the rodent brain, it has been shown that if rAAV is delivered at low infusion rates (<1.0 µl/min), the best transduction levels were obtained. Moreover the vector is delivered with high efficiency to cells immediately surrounding the injection tract, with an exponential fall off in gene expression extending from the tip of the injection cannula. Using volumes of 3 microliters delivering ~5×$10^9$ virions, 80% of transduced cells lie within 1 mm of the injection site with less than 5% of transduced cells lying greater than 2 mm from the injection site. In the study using a 35 µl volume of vector (12 fold greater volume) but a titer approximately 15-20 fold lower (i.e. roughly equivalent number of vector genomes delivered), gene expression was restricted to a volume of several millimeters. This would confine the vector to the STN whose dimensions are approximately 4.8 mm×5 mm×6 mm or ~140 mm.

xi. Efficiency of Transduction

Transduction efficiencies can reach 100% in permissive cell-lines and permissive target cells in vivo if sufficient MOI are used. Based on rodent data it is expected that an injection volume of 35 microliters into a human STN with the absolute number of virion genomic particles of ~3.5×$10^9$ is likely to transduce from 70-175,000 cells. This represents approximately 25-60% of target cells transduced.

xii. Gene Transfer and Expression

With rodent data, using both GAD-65, GAD-67, combinations, as well as HA-tagged GAD-65 and GAD-67, and using injection volumes of 2 µl of vector stocks of approximately 5×$10^{10}$ genomic particles per ml, i.e. a total of $10^8$ vector genomes, approximately 2000 cells in the rodent STN (50,000 vector genomes for 1 neuron transduced) were transduced. This number reflects 15% of the total STN neurons (~13,600 in the rat (Oorshcot (1996) *J Comp Neurol.* 366: 580-99) and is sufficient for both partial behavioral recovery as well as suggestive of neuroprotection as shown by the data. The ratio of expression to vector dose administered appears fairly linear, with 1 neuron transduced for every ~50,000 genomic AAV particles. Hence, to obtain 100,000 transduced STN neurons in the human STN we estimate a vector dose of (100,000 cells×50,000 virions) or 5×$10^9$ vector genomes.

Example 4

In Vitro Expression Studies with rAAV-GAD65 and rAAV-GAD67

HEK 293 cells were plated out at a density of 1×$10^5$ cells/well onto a 24 well plate, 24 hours prior to addition of 5 µl of virus in 100 µl DMEM per well. Forty eight hours later, the cells were processed for immunocytochemistry. The media was aspirated then the cells were washed with 1×PBS. 1 ml 4% paraformaldehyde was added per well and incubated for 15 minutes (min). After aspiration of the 4% PFA, the cells were washed with 1×PBS then briefly incubated in 1% $H_2O_2$ in methanol. The cells were washed in 1×PBS then incubated overnight at room temperature in immunobuffer containing the appropriate dilution of the antibody. (GAD65, Boehringer Mannheim, 1/1000; GAD67, Chemicon, 1/1000). After two five minute washes in 1×PBS, the cells were incubated in immunobuffer containing the appropriate secondary antibody (GAD65, 2 mouse, 1/500. Sigma; GAD67, 2 rabbit, 1/500) for three hours at room temperature. After two five minute washes in 1×PBS, the cells were incubated in immunobuffer containing ExtrAvidin, 1/500, Sigma for two hours at room temperature. After two five minute washes in PBS, the antigen was detected with diaminobenzidine for five minutes where a brown color change indicated the presence of positive cells.

Results

The results showed that GAD65/GAD67 expression was detected after plasmid transfection and virus transduction of HEK 293 cells. No GAD65 or GAD67 was detected in untransfected or untransduced cells. FIGS. 2A and 2D show plasmid transfection of HEK 293 cells with 1 µg of rAAV DNA. FIG. 2B, FIG. 2E show rAAV vector transduction of HEK 293 cells with 5 µl rAAV vector. FIGS. 2C and 2F shows non-transfected HEK 293 cells.

Example 5

GABA Release from Primary Cultured Striatal Neurons Transduced with rAAV-GAD Vectors Primary striatal cultures were prepared from day 15 embryos and plated onto poly-1-lysine coated wells of a 24 well plate at a density of 2.5×$10^5$ for striatal culture and 48 hours later, 2 µl of the following viruses was added to each well in triplicate:

AAV/CB-hGAD65-WPRE
AAV/CB-hGAD67-WPRE
AAV/CB-EGFP-WPRE (control virus).

Ten days later the cells were washed five times in PBS then incubated 5 min in 200 µl aCSF. (first wash). This was collected then the cells were incubated in 200 µl aCSF+ 56 mM KCl for 10 mins at 37° C. (high K+). HPLC was performed to determine the amount of GABA released.

Figure 3:
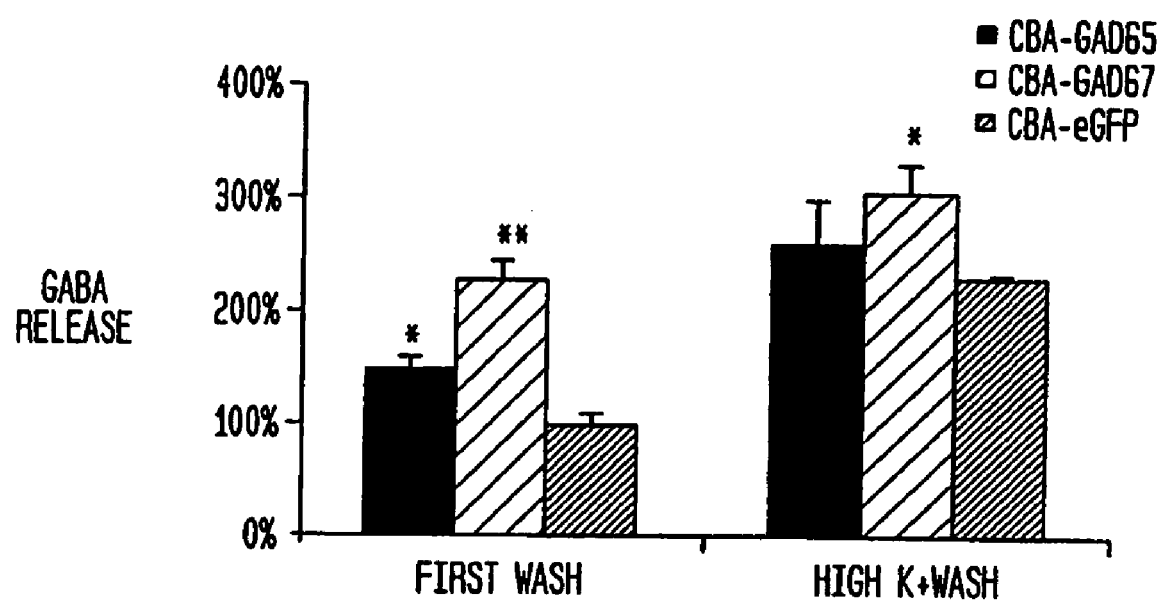
FIG. 3 is a graph showing the effect of rAAV transduction on the GABA release of primary cultured striatal neurons.

The results demonstrated that both GAD67 and GAD65 expression significantly increased the basal and K+-induced release of GABA compared to GFP control (see FIG. 3).

Example 6

In-Vivo Rodent Studies with Neuroprotective and Chronic Lesioned Parkinson's Disease Models Methods a) Animals Male Sprague-Dawley rats (275~325 g) were obtained from Charles River, hosted in standard conditions with constant temperature (22±1° C.) humidity (relative, 30%), 12 hour light/dark cycles (light period 7 a.m./7 p.m.). Animals were allowed free access to food (rodent diet, Labdiet 5001) and water.

b) Surgery

All surgeries were carried out under fresh mixed Ketamine (67 mg/kg)/Xylazine (6.7 mg/kg) (i.p.) injection; animals were mounted in a KOPF 900 series stereotaxic frame. The skull was exposed and a hole drilled above the area of interest. Each intracerebral injection was made by stereotaxic infusion through a 26-gauge stainless steel needle with 10 l Hamilton syringe and a microsyringe pump (World Precision Instruments).

c) Unilateral Lesion of the Medial Forebrain Bundle (MFB):

Hemiparkinsonian rat models were generated by 6-Hydroxydopamoine (6-OHDA) lesion of the left MFB. Thirty minutes before lesioning the animals were injected with desipramine (10 mg/kg, s. c.) (Sigma) (A noradrenaline uptake inhibitor to minimize damage to noradrenergic neurons). Each animal received a unilateral injection of 8 μg/4 μl sterile 6-hydroxydopamine HCl (Sigma) with 0.1% ascorbic acid (Sigma) into the left MFB at coordinates −2.2 mm from Bregma, 1.5 mm from the midline, and 7.8 mm below the dura, with the incisor bar placed at +5 mm above horizontal zero. The injection was made over a 4-min period (1 μl/min). The needle was left in situ for an additional 5 minutes before removal.

d) rAAV Vector Transduction into the Subthalamic Nucleus (STN):

High titer vectors were used in the intra-STN transduction. The concentrates or vectors were: rAAV CBA-hGAD65-WPRE-BGH ($6 \times 10^{10}$ particles/ml), rAAV CBA-hGAD67-WPRE-BGH ($5 \times 10^{10}$ particles/ml), and rAAV CBA-EGFP-WPRE-BGH ($5 \times 10^{5}$ particles/ml).

To enhance the gene expression, combined injection of rAAV with mannitol (21 μl:1 μl) were used. A total volume of 3 μl rAAV vectors or control vector (saline) were injected into the ipsilateral (left) STN at coordinates −3.8 mm from Bregma, 2.4 mm from the midline, and 7.7±0.1 mm below the dura, with the incisor bar placed at 3.5 0.3 mm below the horizontal zero. The intracerebral vector injection was perfused at the rate of 0.2 μl/min. The needle was left in situ for an additional 5 min before removal.

e) Ibotenic Acid-Lesion of the Subthalamic Nucleus (STN):

Since deep brain stimulation (DBS) and direct lesions of STN both have shown ameliorate the cardinal symptoms in clinical and preclinical studies, ibotenic acid-lesion of the STN group were used to compare the therapeutic efficiency of rAAV-GAD transduction of STN neurons. Ibotenic Acid solution (3 μg/1.5 μl, dissolved in 10 mM phosphate-buffered saline, pH adjusted to 7.4 with NaOH) was injected into the ipsilateral STN, using the following stereotaxic coordinates: −3.8 mm from the bregma, 2.4 mm lateral to the midline, and 7.7±0.1 mm from the dural surface. The intracerebral infusion was administered at the rate of 0.2 μl/min, and the needle was left in situ for an additional 5 min before removal.

f) Behavioral Tests i) Apomorphine-Induced Rotation

Rats were tested for rotational behavior induced by apomorphine. For each test, the rat was injected apomorphine hydrochloride (0.1 mg/kg, s. c.) (Sigma) dissolved in sterile 0.1% ascorbate-saline, and 15 min after injection each animal was placed into the 60 cm-diameter hemispherical bowls and the total number of contralateral rotations over 5 mins were counted. The first rotation test began at three weeks after the 6-OHDA-lesion of MFB, and the following tests were performed every three weeks. 6-OHDA-lesioned animals showing apomorphine-induced rotations less than 15 in the total 5 min test were removed from the gene therapy of chronic PD group.

ii) Head Position

The position of the head relative to the body axis was measured before the surgeries, and every three weeks after the lesion and rAAV transduction till the end of the experiment. The rats were placed in the standard trays, allowed to habituate freely, and the position of the head (>10 deviation left or right of the midline, or neutral) was counted in 60 seconds (sec). The ipsilateral head position bias of unilateral parkinsonian rats were analyzed using the mean percentage the head was oriented in the ipsilateral, contralateral or neutral direction at 2 and 4 months after the vector transdution.

iii) Paw Touching

The paw-touching test assesses the independent use of the forepaws for touching movements. Rats were placed in plastic cylinders (height 30 cm, diameter 25 cm). The number of times the rat rose up and touched the wall of the cylinder with either left, right or both forepaws was counted in a 3 min test. The decreased paw touching movements and bias of unilateral parkinsonian rats were analyzed at 2 and 4 months after the vector transduction.

iv) Locomotor Activity

Locomotor activity of each animal was measured at 3 and 6 months after vector transduction using MED Associate Activity Monitors (ENV-515). On test days each rat was placed individually inside a polycarbonate activity monitor chamber (17×17×12 inches). Activity was monitored by infrared light beam sensors (sixteen beams per side) located in the X, Y, and Z planes. Distance traveled was measured at 5 min intervals for sixty minutes with a Pentium II PC computer and Activity Monitor software (Version 4). The mean distance traveled in the 60 min period was then analyzed.

g) In Vivo Substantia Nigra Electrophysiology During STN Stimulation

Ten male Sprague-Dawley rats (450-700 g) were used in these experiments. Animals were initially anesthetized with 3% halothane; 1.5% halaothane was maintained during surgery and the experiment to maintain a deep and constant level of anesthesia as determined by lack of movement to a strong tail pinch. Animals were placed in a stereotaxic instrument (Cartesian Research) with the incisor bar angled to establish a flat head between lamba and bregma. Body temperature was maintained at 37° C. with a Thermistor-controlled heating pad (FHC, Inc.).

(h) Subthalamic Nucleus (STN) Stimulation Electrode Implantation:

The tissue at the rostral skull margin was reflected and cranial bones were partially removed. Placement of stimulation electrodes in STN was accomplished using streotaxic coordinates (−0.6 mm Bregman, 2.6 mm lateral to midline, 15 degree angle, 8.1 mm deep). Stimulation electrodes consisted of a pair of twisted 150 micro diameter stainless steel wires, insulated except for bluntly cut tips. Electrical stimuli were unipolar pulses (0.5 ms duration) from a square wave stimulator (AMPI, Master 8) and a constant current stimulus isolation unit (AMPI, Iso-Flex). Logic pulses synchronized with STN stimulation were led to a computer for on-line peristimulus time histogram (P5TH) generation.

(i) Substania Nigra (SN) Recordings

A 3 mm diameter hole was drilled in the skull above the SN (5.3 mm caudal to bregma and 2.2 mm lateral to midline), and the dura was reflected. Extracellular recordings from individual neurons were obtained with glass micropipettes (2-4 μm tip diameter, 10-20 MOhm impedance) filled with 1% Pontamine sky blue dye in 0.5M sodium acetate, 0.5M NaCl. Recordings were obtained and processed by standard electrophysiological methods. Baseline spontaneous discharge was monitored for 1-3 min and collected on-line by computer. Neuronal responses to single-pulse STN stimulation were examined and threshold for synaptic activation (driving on approximately half the stimuli) was determined. PSTHs of SN responses to STN stimulation for at least 30 consecutive stimulus trials presented at 1/s (up to 5 mA).

(j) Data Analysis

Spontaneous spike discharge rates were calculated from computer records averaged over 1 min. To quantify the effects of STN stimulation, individual PSTHs were analyzed by computer to determine excitatory and inhibitory epochs. A baseline period was defined as the 200 ms epoch preceding stimulation, and the mean and standard deviation of counts per baseline bin were determined. The onset of significant excitation was defined as the first of 5 consecutive bibs (10 ms bin width) whose mean value exceeded mean baseline activity by two standard deviations.

(k) In Vivo Substantia Nigra Microdialysis During STN Stimulation

The experiments were carried out at four to five months after the vector transduction into the STN. The rats weighed between 550-650 g. Animals were anaesthetized with isoflurane with oxygen and placed in the stereotaxic apparatus (Anilam, Cartesian Research, INC.)

(l) STN Stimulation

The stimulator was placed at the coordinates: −0.6 mm from bregma and 2.6 mm from the midline, and the stimulator was inserted 8.2±0.1 mm from the dura with an angle of 15 degrees from dorsal to ventral. Stimuli were delivered by an AMPI accupulser (Master-8, AMPI) and stimulus isolation units (ISO-Flex, AMPI) which gave a rectangular pulse. Low and high frequency stimulation (LFS, HFS) parameters used were: frequency, 10 Hz; pulse width, 500 µs; intensity 500 µA for STN-LFS; and frequency, 130 Hz; pulse width, 500 µs; intensity 500 µA for STN-HFS.

(m) Substantia Nigra Microdialysis

CMA microdialysis probes were customized with an active dialyzing membrane length of 0.5~0.7 mm especially for microdialysis in small regions. The probe membrane (cuprophane) had a molecular weight cut off of 6000 Dalton and the outer diameter of the probe was 0.24 mm. When inserted, the tip of the microdialysis probe was placed into the SN: −5.8 mm from bregma, 2.4 mm from midline and 8.3±0.2 mm ventral from dura matter.

Probes were inserted 2~3 hours before the microdialysis study, connected using vitreous silica tubing (1.2 µl/100 mm) to 1-mil glass syringes mounted on a CMA/100 Microinjection Pump. The dialysis system was perfused at 1.0 µl/min with sterilized, pyrogen-free artificial extracellular fluid (aECF) (composition in mmol/L: NaCl, 135; KCl, 3; $MgCl_2$, 1.0; $CaCl_2$, 1.2; ascobate, 0.2 and 2 mM sodium mono- and dibasic phosphate to pH 7.4). The collection period was 5 min during the STN stimulation.

At the end of experiments, the microdialysis probes were removed and stored in distilled water between experiments. The animals were anaesthetized with Euthasol and perfused intracardially with 0.01M phosphate-saline buffer followed by 4% paraformaldehyde. The brain was removed and cut into 20 µm sections using freezing cryostat. Cresyl violet staining was performed to check the position of the microdialysis probes and the stimulation electrode. All animals presenting misplaced microdialysis probes or stimulation electrode were eliminated.

(n) Chromatographic Method for Amino Acid Analysis

The amino acids content of each sample (specifically GABA and Glutamate) was analyzed by using a binary gradient high-performance liquid chromatography (HPLC) (Shimazu) with fluorescence detection and pre-column derivatization O-phthalaldehyde (OPA) (obtained from Pierce). A sample to reagent ratio of 1:3 (v/v) was used (5 µl dialysate sample+15 µl OPA). After a 60 second reaction, 15l of each sample was auto-injected into the column (100×3, 3 µm, 120A, Keystone). The mobile phases used for separation were A: 0.03M sodium acetate, 1.0% tetrahydrofuran solution (pH 6.88) and B: 0.02M sodium acetate, 80.0% acetonitrile solution (pH 6.82).

(o) Histology

Approximately 4-5 months after the rAAV transduction, the animal were deeply anaesthetized with Euthasol and perfused intracardially with 0.01M phosphate-saline buffer followed by 4% paraformaldehyde. The brain was removed and placed into 4% paraformaldehyde solution about 4 hours and then transferred to 20% and 30% sucrose solution for 48 hours. Coronal 20 µm tissue sections were cut at −20° C. using a freezing cryostat (Leica, Germany) at the pallidal, subthalamic and nigra levels.

(p) Real Time Quantitative RT-PCR for gene expression 3-4 months after rAAV transduction, animals were anesthetized with Euthasol and the brains were removed quickly. Bilateral STN, Nigra and GPe were dissected. Total RNA was isolated from each brain regions using TRIzol reagent (Life Technologies, Inc) as per the manufacturer's protocol. Before RT-PCR, RNA was incubated with RQ DNase (RNase free) for 30 min at 37° C. followed by heat denaturation for 5 min at 75° C.

The mRNA for WPRE was measured by real-time quantitative RT-PCR using PE Applied Biosystem prism model 7700 sequence detection system. The sequences of forward and reverse primers were 5'-TGGCGTGGTGTGCACTGT-3' (SEQ ID NO: 15) and 5'-GTTCCGCCGTGGCAATAG-3' (SEQ ID NO: 16) respectively. The WPRE Taqman fluorogenic probe was 5'-6FAM-TCCGGGACTTTCGCTTTC-CCCC-TAMRA-3' SEQ ID NO: 17).

The mRNA for GAPDH in each sample was used as the endogenous control to normalize quantitation of hGAD65/67 mRNA for difference in the amount of total RNA added to each reaction. Taqman rodent GAPDH control kit from PE Applied Biosystem was used. The sequences of primers and probe are company's proprietary. RT-PCR was done in two-steps as per company's protocol. Targets and endogenous control were run in the same tube with different reporter dyes. Delta Ct represents WPRE threshold cycle nomalized to GAPDH (ΔCt=Ct WPRE-Ct GAPDH).

(q) Statistical Analysis

Statistical analysis was performed on the data using the STATVIEW program for ANOVA and t-test.

(r) Summary of Experimental Design i) Gene Therapy of Chronic PD Study 1

In this study, rAAV were administrated three to four months after the 6-OHDA unilateral lesion of MFB. Animals were grouped equally according to the stable baseline apomorphine-induced rotation data as shown in Table 1.

TABLE 1

| Groups | Number | AAV Injection site | Dose AAV + mannitol | Survival after AAV injection |
|---|---|---|---|---|
| NSE-rGAD65 | n = 10 | ipsi STN | 2 µl + 1 µl | 10 months |
| NSE-rGAD67 | n = 10 | ipsi STN | 2 µl + 1 µl | 10 months |
| NSE-rGAD65&67 | n = 10 | ipsi STN | 2 µl + 1 µl | 10 months |
| NSE-EGFP | n = 10 | ipsi STN | 2 µl + 1 µl | 10 months |
| PBS control | n = 5 | ipsi STN | 2 µl + 1 µl | 10 months |
| CBA-hGAD65 | n = 10 | ipsi STN | 2 µl + 1 µl | 8 months |
| empty rAAV | n = 8 | ipsi STN | 2 µl + 1 µl | 14 months | ii) Gene Therapy on Chronic PD Study 2

In this study, rAAV were administered three months after the 6-OHDA unilateral lesion of MFB. Animals were grouped equally according to the stable baseline apomorphine-induced rotation data as shown in Table 2.

TABLE 2

| Groups | Number | AAV Injection site | Dose AAV + mannitol | Survival after AAV inj. |
|---|---|---|---|---|
| CBA-hGAD65 | n = 10 | ipsi STN | 2 μl + 1 μl | 5 months |
| CBA-hGAD67 | n = 10 | ipsi STN | 2 μl + 1 μl | 5 months |
| CBA-hGAD65&67 | n = 10 | ipsi STN | 1 μl + 1 μl + 1 μl | 5 months |
| Ibotenic acid | n = 10 | ipsi STN | 2 μl + 1 μl | 5 months |
| Chronic PD | n = 20 | | | | iii) rAAV Neuroprotective Study

In this study, rAAVGAD65/67 were administered three weeks prior to the 6-OHDA ipsilateral lesion of MFB. Groups are shown in Table 3.

TABLE 3

| Groups | Number | AAV Injection site | Dose AAV + mannitol | Survival after AAV inj. |
|---|---|---|---|---|
| CBA-hGAD65 | n = 13 | ipsi STN | 2 μl + 1 μl | 7 months |
| CBA-hGAD67 | n = 10 | ipsi STN | 2 μl + 1 μl | 2 months |
| CBA-HA-hGAD65 | n = 7 | ipsi STN | 2 μl + 1 μl | 6 months |
| CBA-HA-hGAD67 | n = 8 | ipsi STN | 2 μl + 1 μl | 6 months |
| CBA-GFP | n = 8 | ipsi STN | 2 μl + 1 μl | 6 months |
| Saline | n = 12 | ipsi STN | 2 μl + 1 μl | 6 months |

HA-GAD65/67 refers to the addition of an HA epitope tag to the N-terminus of the protein which allowed immunohistochemical detection of recombinant GAD65/67 to be distinguished from the endogenous protein.

(s) Results i) Behavioral Testing

Apomophine-Induced Rotational Asymmetries

Figure 4:
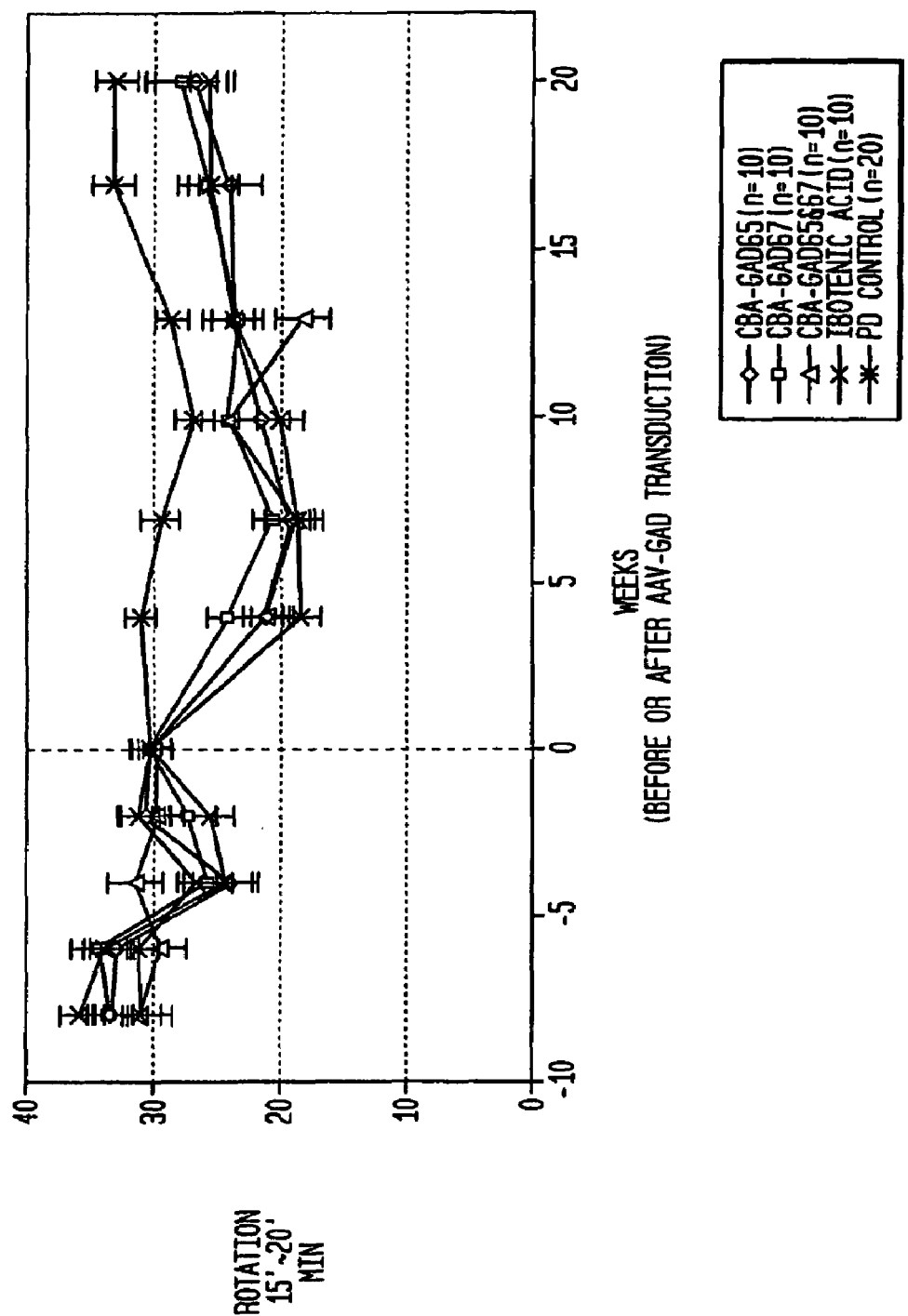
FIG. 4 is a graph showing the effect of rAAV-GAD treatment on apomorphine-induced rotation in chronic Parkinson's Disease Rats.

In the chronic Parkinson's Disease study, rAAV-GAD treatment groups showed reduced rotations under apomorphine compared to the progressive PD group, which was similar to the ibotenic acid lesioning of STN. FIG. 4 is a graph showing the effect of rAAV-GAD treatment on apomorphine-induced rotation in chronic Parkinson's Disease Rats.

Figure 5:
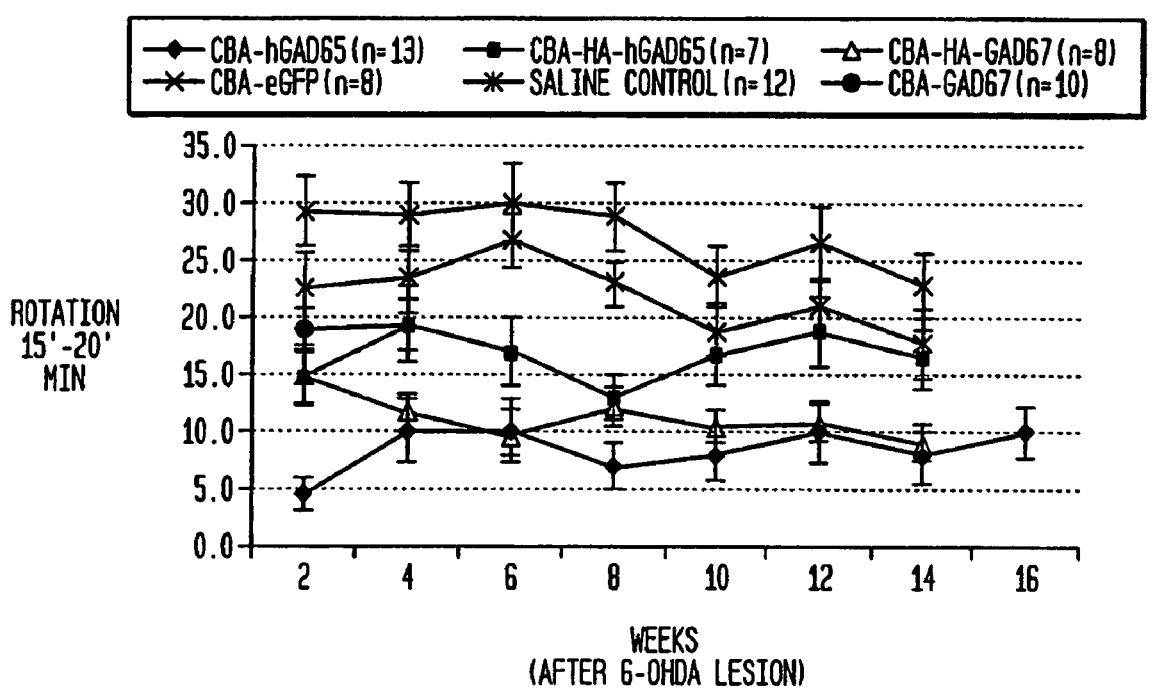
FIG. 5 is a graph showing the neuroprotective effect of rAAV-GAD treatment on apomorphine-induced rotation.
Figure 6A:
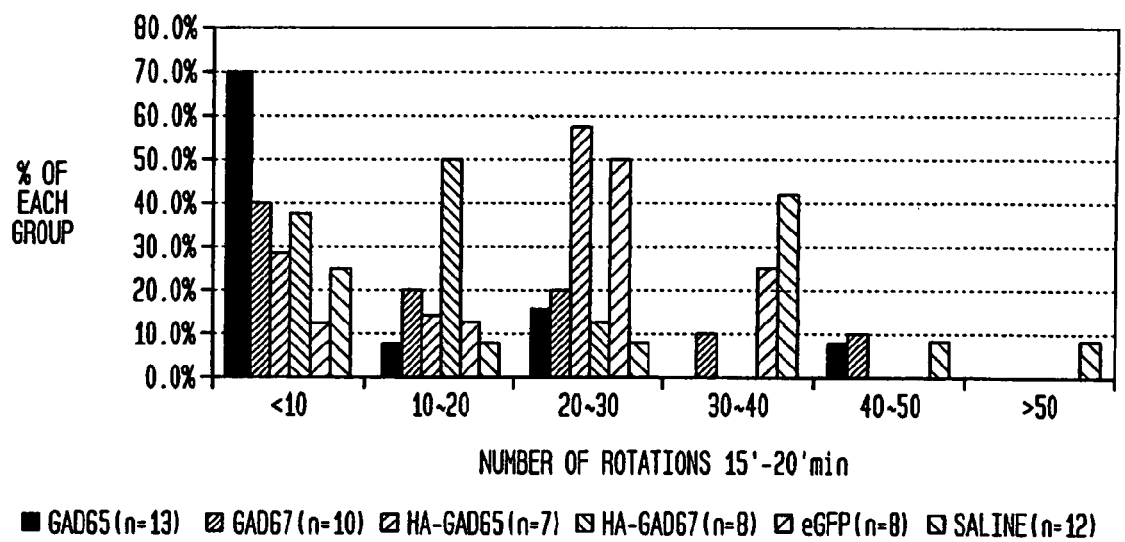
FIG. 6A is a graph showing the potent neuroprotective effect of GAD65 on apomorphine rotation.
Figure 6B:
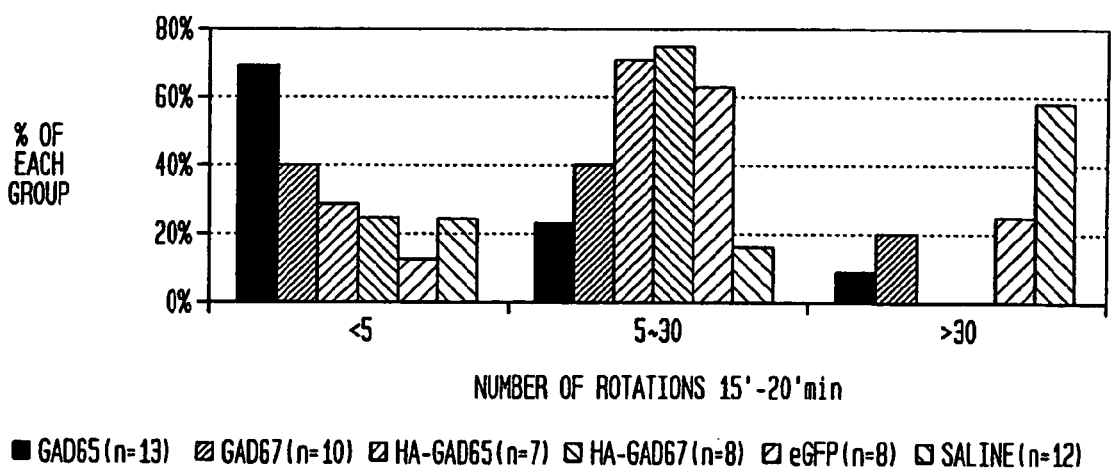
FIG. 6B is another graph showing the potent neuroprotective effect of GAD65 on apomorphine rotation.

In neuroprotective study, all rats administered rAAV-GAD65/67 showed protection against 6-OHDA insult. FIG. 5 is a graph showing the neuroprotective effect of rAAV-GAD treatment on apomorphine-induced rotation. Rats with rAAV-GAD65 showed the best protective effect, over 69% rats showed absolutely no rotational asymmetry. FIGS. 6A and 6B are graphs showing the neuroprotective effect of rAAV-GAD treatment on apomorphine-induced rotation. Collectively, this data shows that GAD65 and GAD67 injected animals displayed a decrease in apomorphine induced rotations over 15-20 mins.

Head Position

Figure 7A:
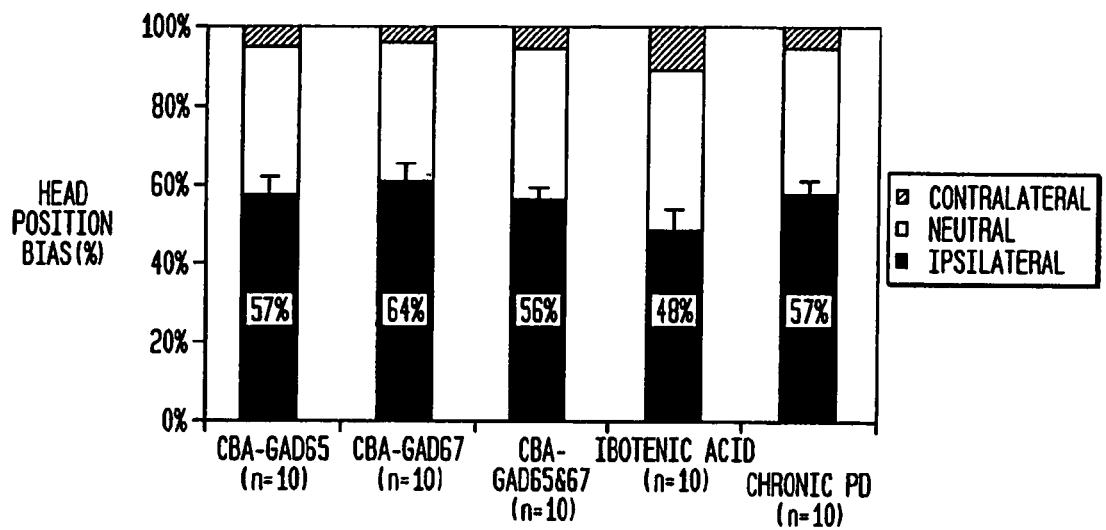
FIG. 7A is a graph showing that there was no significant reduction in head position bias 2 months after rAAV transduction in chronic Parkinson's Disease Rats.
Figure 7B:
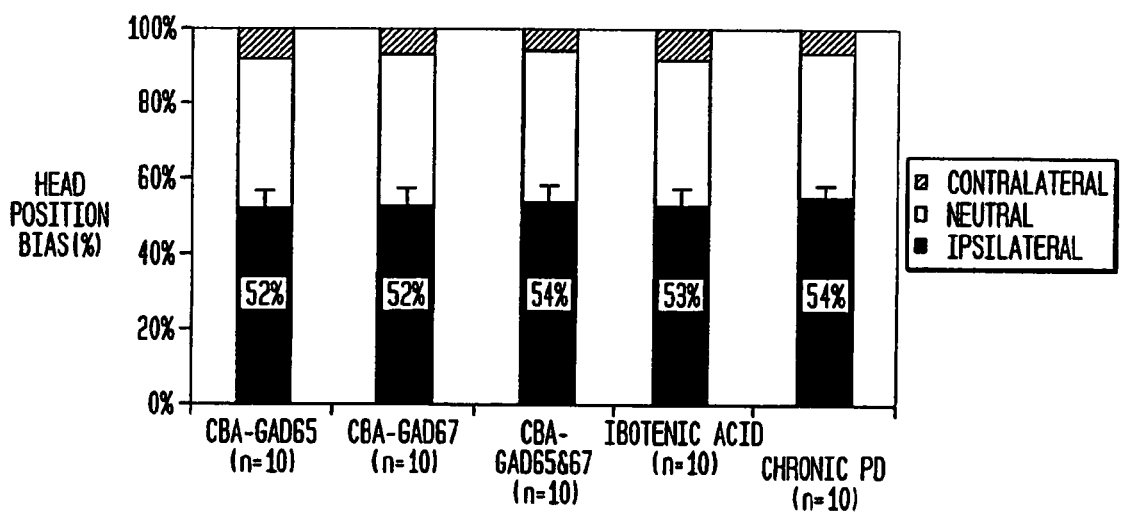
FIG. 7B is a further graph showing that there was no significant reduction in head position bias 4 months after rAAV transduction in chronic Parkinson's Disease Rats.
Figure 8A:
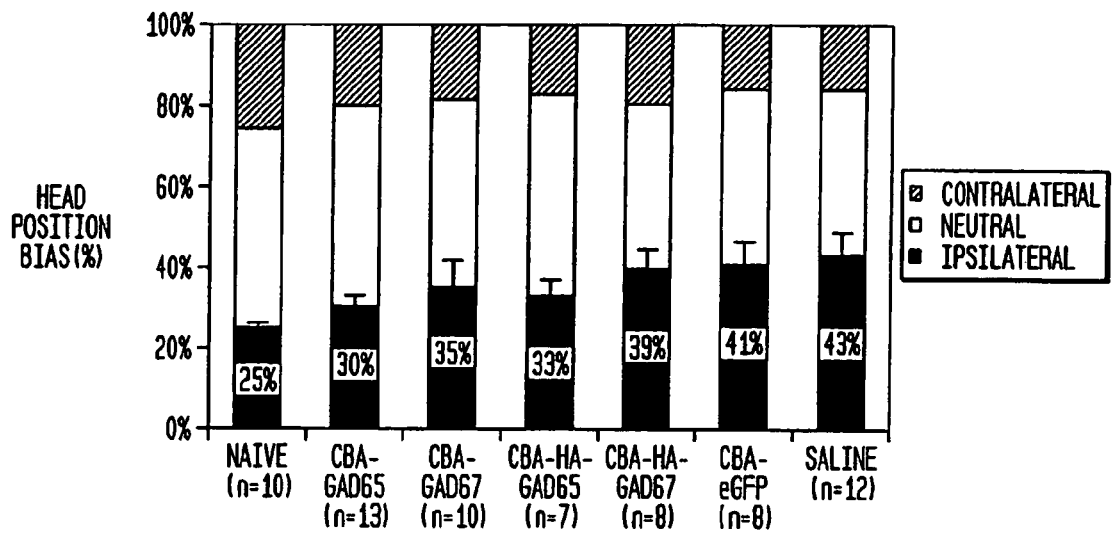
FIG. 8A is a graph demonstrating that head position bias was improved in rats transduced with rAAV-GAD65.
Figure 8B:
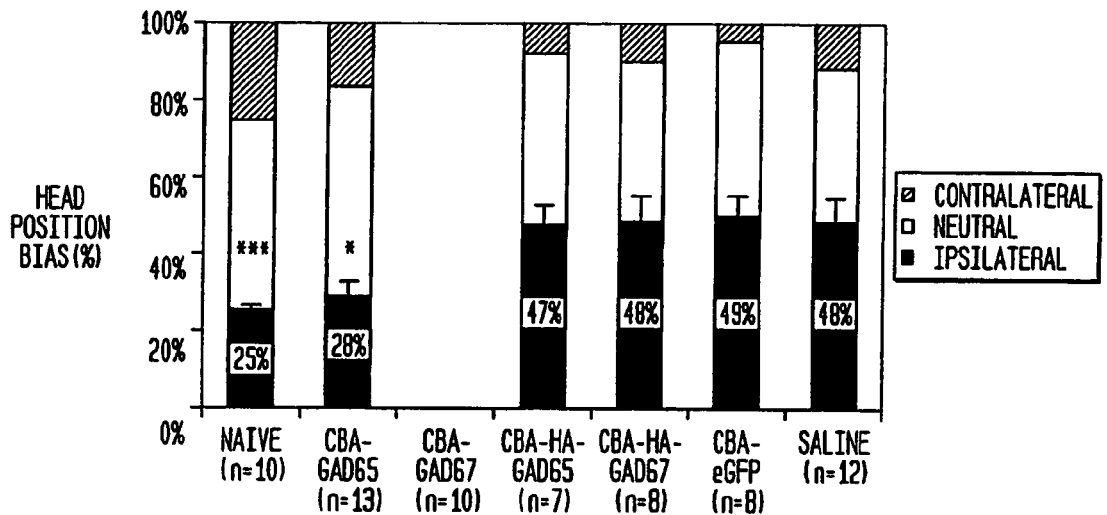
FIG. 8B is a further graph showing that rAAV-GAD65 transduced rats showed marked effects on head position bias.
Figure 9:
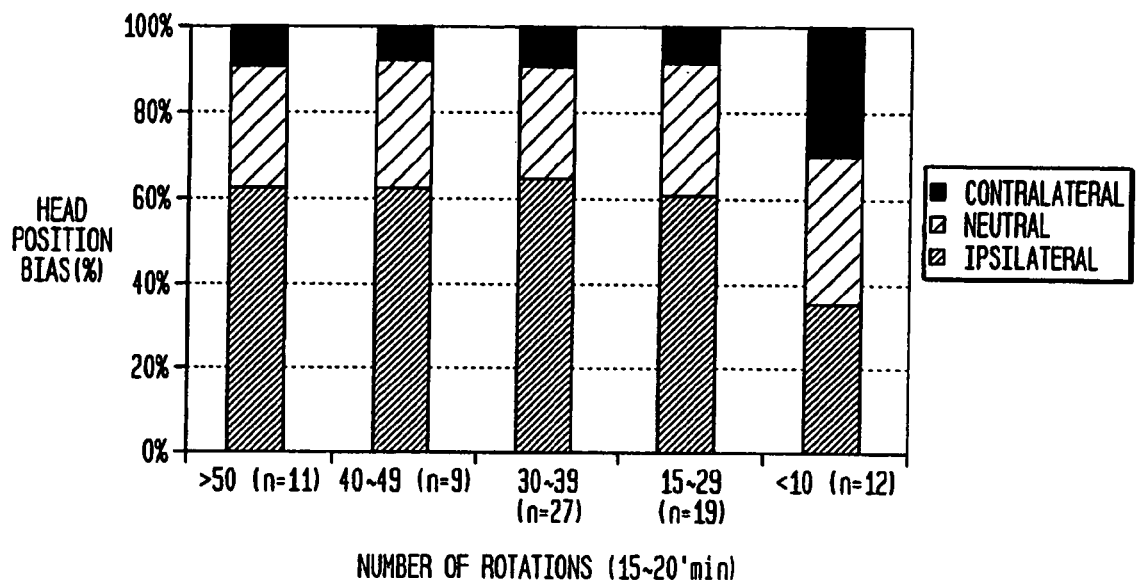
FIG. 9 is a graph demonstrating a direct correlation between apomorphine rotation and head position bias.

The 6-OHDA lesion induced ipsilateral bias. This was used as one the quantitive markers of the parkinsonian phenotype. No significant reduction in 6-OHDA lesion induced ipsilateral head position bias was observed in a rAAV-GAD65, 67 or 65 and 67 administered chronic hemiparkinsonian rats (FIGS. 7A and 7B). However, in rats with rAAV-GAD65, this symmetry bias was much improved (FIGS. 8A and 8B). The GAD67 group was not tested at 14 weeks. FIG. 9 is a chart showing there is a direct correlation between apomorphine rotation and head position bias.

Paw Touching

Figure 10:
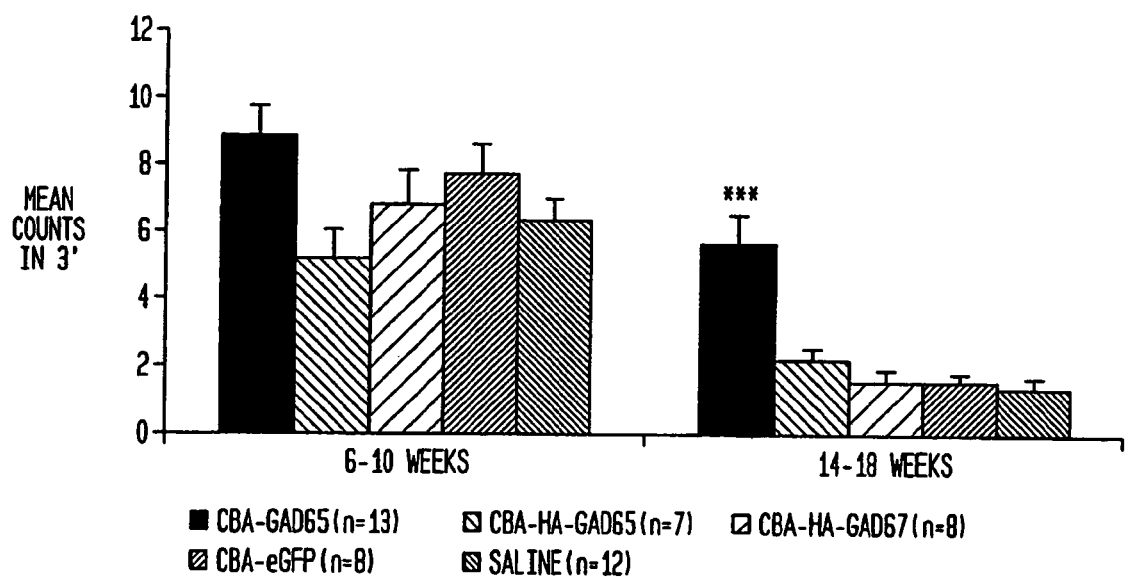
FIG. 10 is graph showing that paw touching counts were significantly improved in all rAAV-GAD and Ibotenic acid lesion groups.

The 6-OHDA lesion induced a decreased forepaw rising and touching movement as well as an ipsilateral bias. Forepaw touching movement was significantly improved in all rAAV-GAD and Ibotenic acid lesion groups of Chronic PD rats. FIG. 10 is a chart showing paw touching counts were significantly improved in all rAAV-GAD and Ibotenic acid lesion groups. The GAD65/67 group was not tested at 14 weeks. Prior administration of rAAV-GAD65 effectively protected against the loss of paw touching movement induced by MFB 6-OHDA lesioning. FIG. 11 is a chart showing rAAV-GAD-65 had a marked neuroprotective effect on paw touching counts.

Locomotor Activity

Figure 12A:
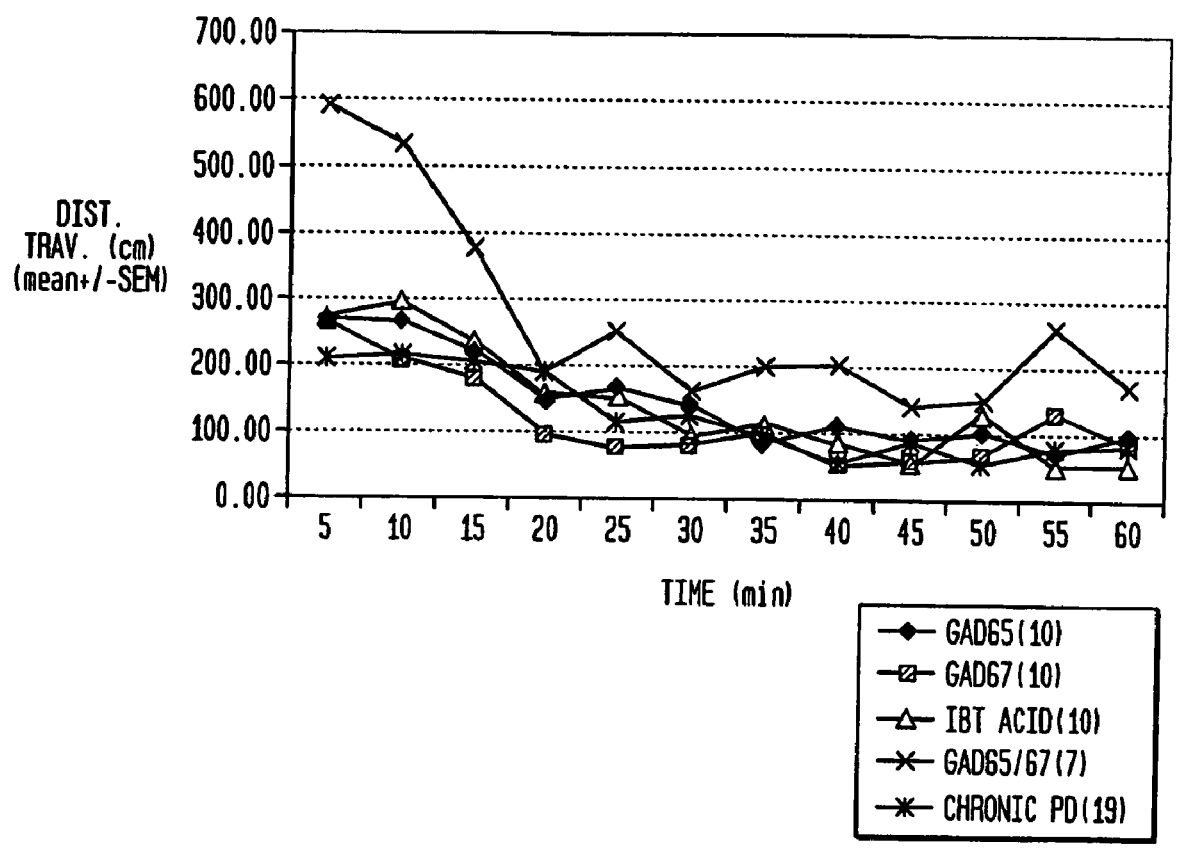
FIG. 12A is a graph demonstrating that a marked improvement in locomotor activity was observed in Parkinson's Rats with combined rAAV-GAD65 and 67.
Figure 12B:
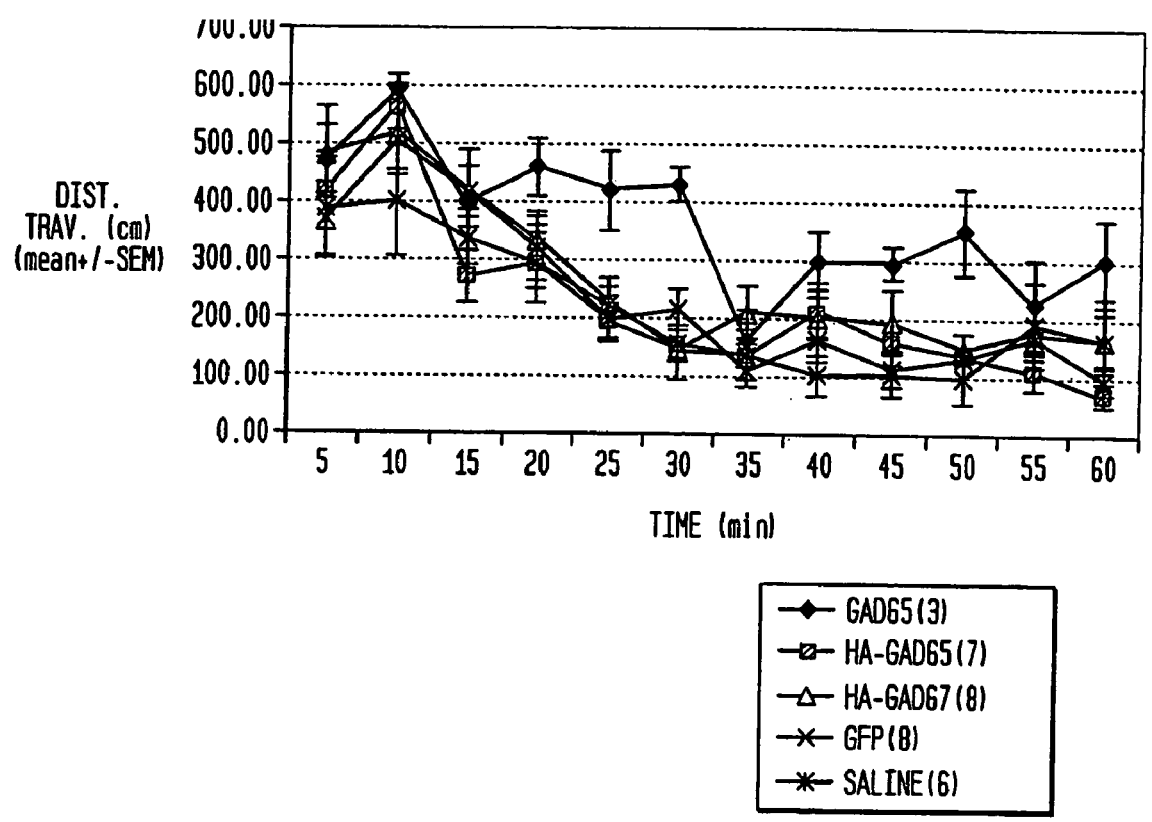
FIG. 12B is a another graph further demonstrating that a marked improvement in locomotor activity was observed in Parkinson's Rats with combined rAAV-GAD65 and 67.

The horizontal locomotor activity decreased progressively in chronic Parkinson's rats. Combined rAAV-GAD65 and 67 transduced rats showed marked improvements in their locomotor function. FIGS. 12A and 12B are graphs showing a marked improvement in locomotor activity was observed in Parkinson's Rats with combined rAAV-GAD65 and 67.

Figure 13A:
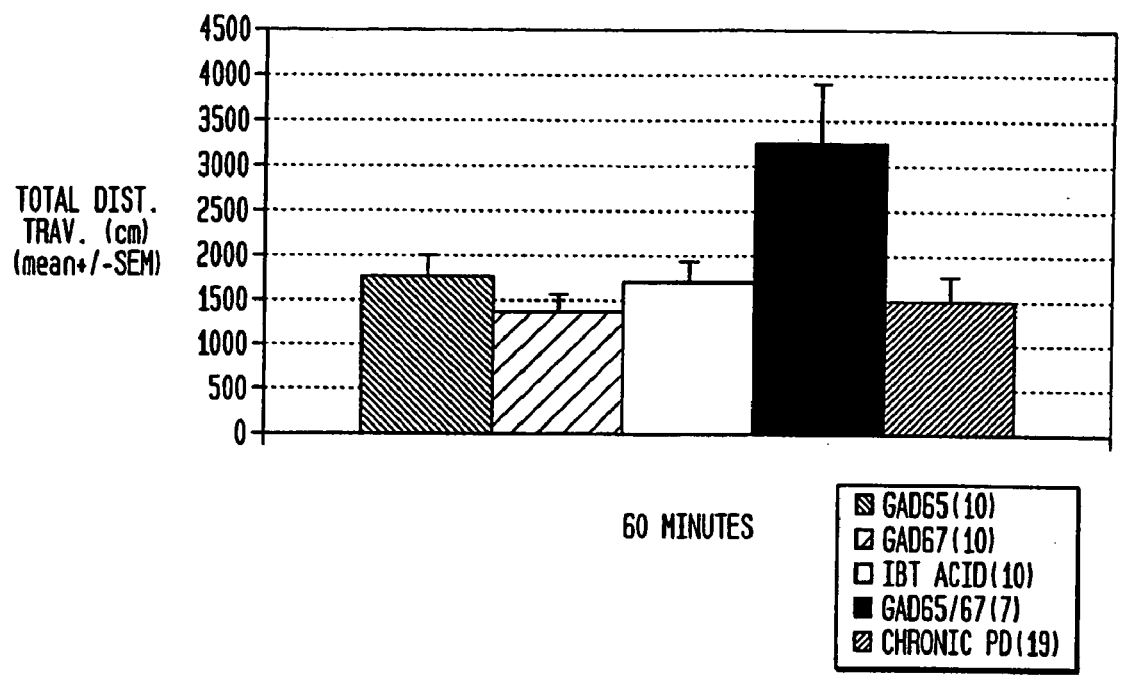
FIG. 13A is a graph showing that there was also evidence of neuroprotective effects on locomotor activity by rAAV-GAD transduction.
Figure 13B:
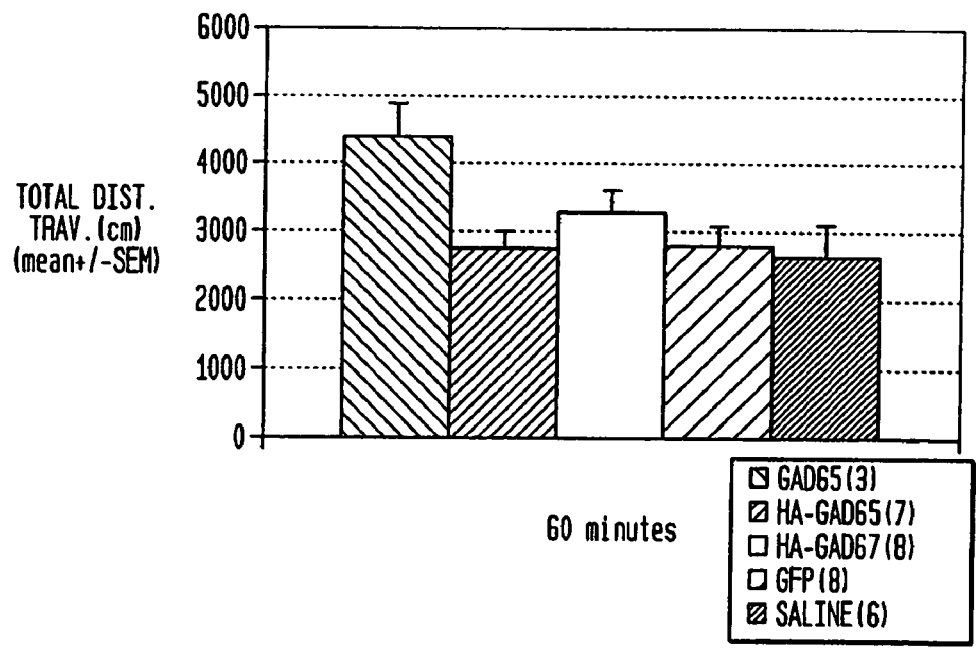
FIG. 13B is a graph further showing a neuroprotective effects on locomotor activity by rAAV-GAD transduction.

Prior administration of rAAVGAD65 also protected effectively against the reducing horizontal locomotor activity induced by MFB 6-OHDA lesion. FIGS. 13A and 13B are charts showing there was evidence of neuroprotective effects on locomotor activity by rAAV-GAD transduction.

ii) In Vivo Substantia Nigra Electrophysiology During STN Stimulation

Electrophysiology and microdyalisis was performed in the substantia nigra (SN) of normal rats and rats treated with the CBA-GAD65 virus containing human glutamic acid decarcoxylase (GAD65/67) which converts glutamate to GABA in neurons. In rats that received the virus, 6-OHDA lesions of the medial forebrain bundle were performed three weeks after the virus was injected into the subthalamic nucleus (STN) to model the degeneration of dopamine neurons in PD. Electrophysiology and microdyalisis was performed at least 4 months after the transduction of the virus.

Figure 14:
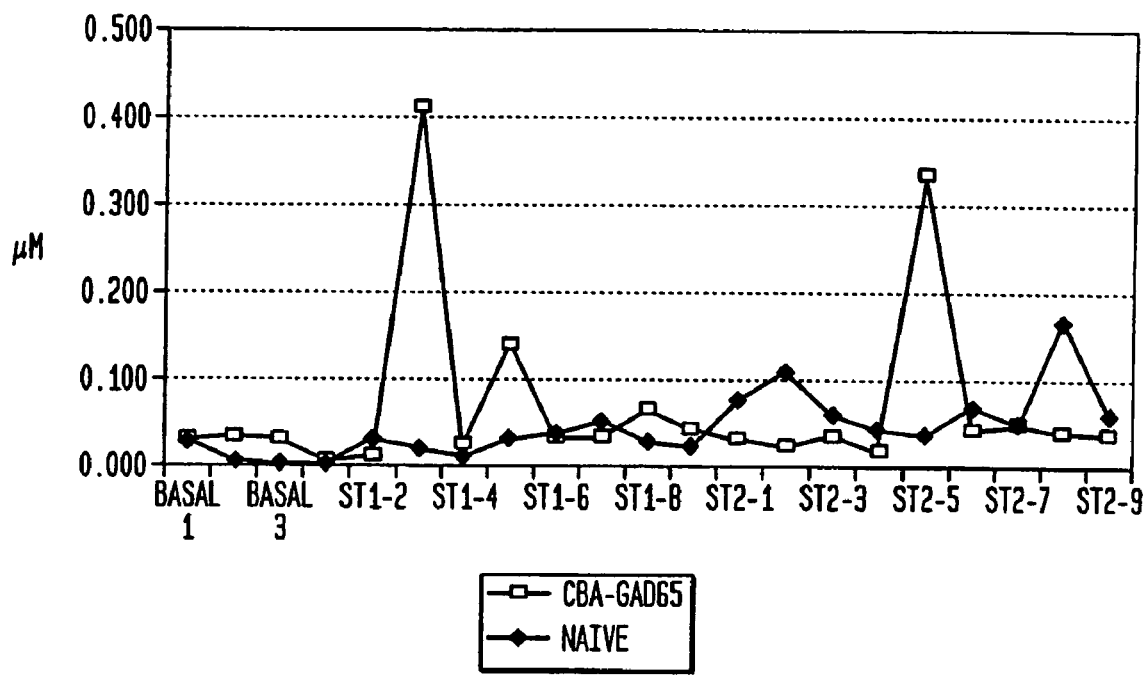
FIG. 14 is a graph of extracellular GABA Concentration during STN Stimulation.
Figure 15:
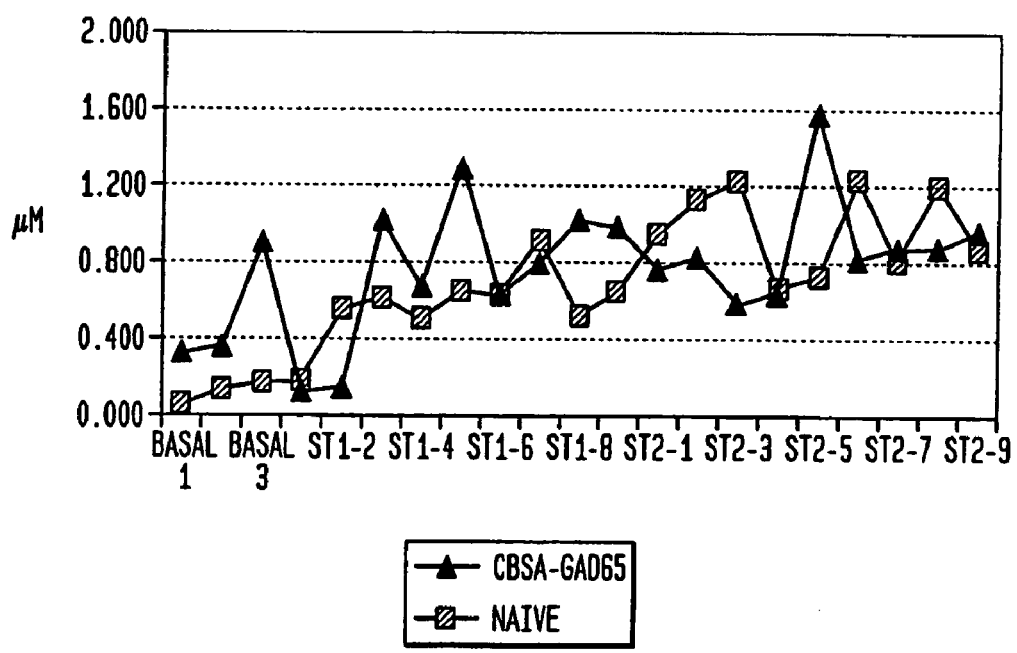
FIG. 15 is a graph of Extracellular Glutamate Concentration during STN Stimulation.

Inhibitory GABA containing connections were detected from the STN to the SN using electrophysiology and microdialysis. In the microdialysis experiments, a 10× increase in GABA was detected due to low frequency electrical stimulation of the STN, compared to a 3× increase in control rats. Table 4 for GAD rat #304 and for control rat # 217 shows the concentration of GABA, glutamate and aspartate in the SN obtained before and after low frequency stimulation. The sample labels are Basal #, for the samples taken before stimulation, ST1-#, for successive samples after the first low frequency stimulation for 2 minutes and ST2-#, for successive samples after the first low frequency stimulation for 5 minutes. FIGS. 14 and 15 are charts showing extracellular GABA concentration during STN stimulation and correspond to the GABA and glutamate data in Table 4.

TABLE 4

SN Microdialysis during STN stimulation.
Substantia Nigra Microdialysis During the
Subthalamic Nucleus Stimulation

|  |  | GAD65 | | Naïve | |
|---|---|---|---|---|---|
| Sample 5 ul/15 ul | Flow Rate (1.0 ul/min) | GABA uM | Glu uM | GABA uM | Glu uM |
| Basal 1 |  | 0.031 | 0.351 | 0.027 | 0.056 |
| Basal 2 |  | 0.033 | 0.328 | 0.007 | 0.133 |
| Basal 3 |  | 0.030 | 0.357 | 0.004 | 0.168 |
| ST1-1 | LFS-1: 10 Hz, 500 uA for 2' | 0.006 | 0.125 | 0.004 | 0.178 |
| ST1-2 |  | 0.010 | 0.143 | 0.031 | 0.553 |
| ST1-3 |  | 0.410 | 1.008 | 0.021 | 0.606 |
| ST1-4 |  | 0.026 | 0.673 | 0.011 | 0.501 |
| ST1-5 |  | 0.139 | 1.290 | 0.032 | 0.644 |
| ST1-6 |  | 0.033 | 0.624 | 0.037 | 0.623 |
| ST1-7 |  | 0.034 | 0.787 | 0.052 | 0.904 |
| ST1-8 |  | 0.065 | 1.009 | 0.027 | 0.514 |
| ST1-9 |  | 0.043 | 0.976 | 0.023 | 0.639 |
| ST2-1 | LFS-2: 10 Hz, 500 uA for 5' | 0.032 | 0.758 | 0.078 | 0.938 |
| ST2-2 |  | 0.023 | 0.819 | 0.108 | 1.121 |
| ST2-3 |  | 0.033 | 0.580 | 0.061 | 1.213 |
| ST2-4 |  | 0.016 | 0.629 | 0.043 | 0.661 |
| ST2-5 |  | 0.332 | 1.564 | 0.036 | 0.718 |
| ST2-6 |  | 0.044 | 0.809 | 0.068 | 1.220 |
| ST2-7 |  | 0.049 | 0.863 | 0.049 | 0.796 |
| ST2-8 |  | 0.041 | 0.866 | 0.164 | 1.183 |
| ST2-9 |  | 0.038 | 0.951 | 0.061 | 0.852 |

Note:
each sample was collected every 5-6 min

Figure 16:
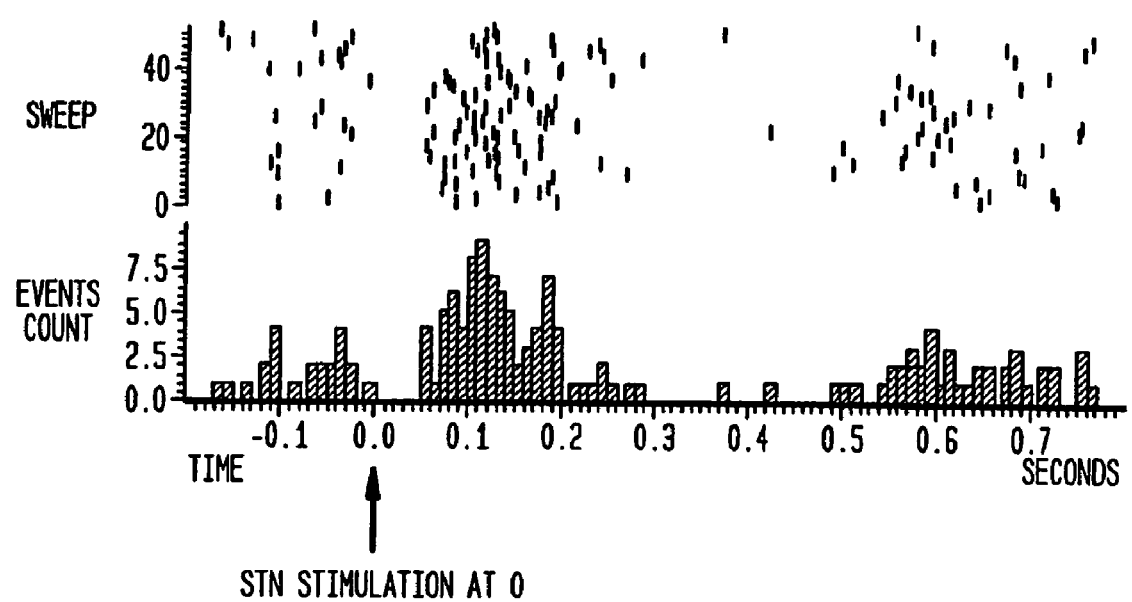
FIG. 16 is a histogram showing the response of neurons in the Substantia Nigra to electrical stimulation in the STN of a normal rat.
Figure 17:
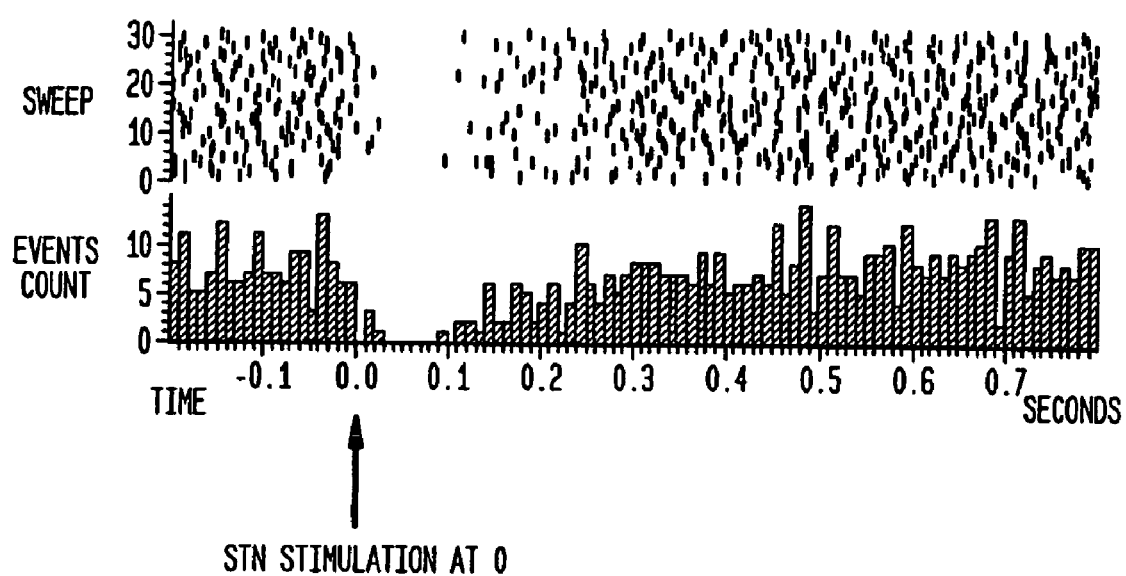
FIG. 17 is a histogram showing the response of neurons in the Substantia Nigra to electrical stimulation in the STN in rAAV-GAD transduced rat.
Figure 18A:
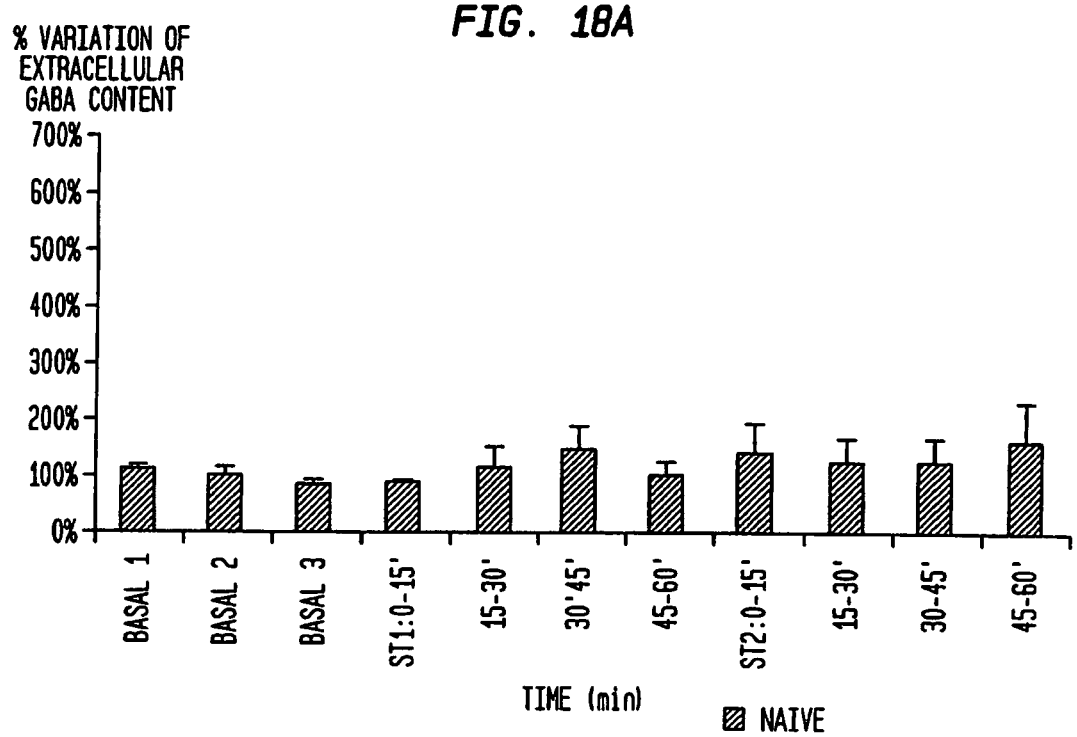
FIG. 18A is a graph of extracellular GABA concentration in the SN during STN stimulation in naïve rats.
Figure 18B:
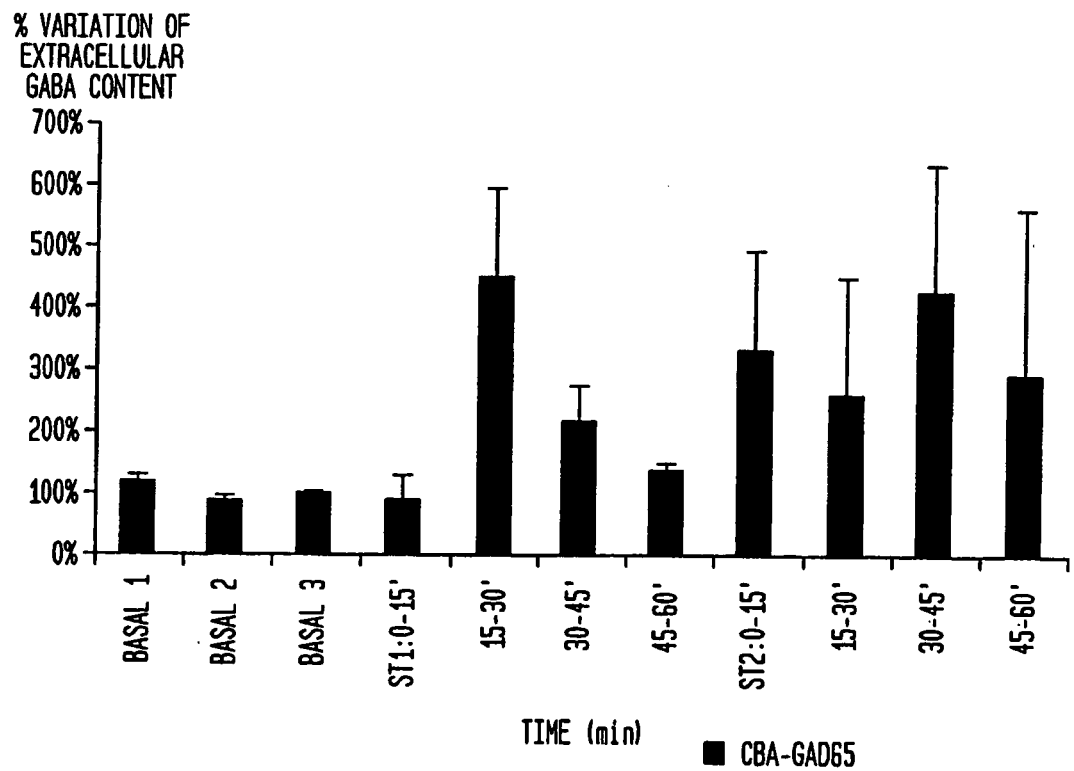
FIG. 18B is a graph of extracellular GABA concentration in the SN during STN stimulation in rAAV-GAD rats.

FIGS. 16 and 17 show the response of neurons in the Substantia Nigra (SN) to electrical stimulation of the STN. These Figures show a histogram (20 ms bins) of spike counts after a electrical stimulation at t=0. Each trial of the stimulation used to create the histogram is included and labeled sweep of the graph. FIG. 16 is a chart showing the response of neurons in the Substantia Nigra to electrical stimulation in the STN of a normal rat and shows that in normal rats there is a large increase in impulse activity due to STN stimulation. FIG. 17 is a chart showing the response of neurons in the Substantia Nigra to electrical stimulation in the STN in rAAV-GAD transduced rat and shows an inhibition of spontaneous firing of the neuron in the SN due to STN stimulation. The stimulation in each of FIGS. 16 and 17 occurred at time=0. The histograms and raster plots shows 200 ms before and 800 ms after the stimulus for comparison of the impulse rate immediately after stimulation.

iii) Extracellular GABA and Glu Concentrations in Substantia Nigra Microdialysis During STN Stimulation The current data show a significant increase in extracellular GABA in GAD65 transduced compared to naïve rats following low frequency stimulation of the STN. There was a 4.4× increase in mean GABA concentration during the first 15 min fractions after the LFS in GAD65 transduced group, compare to a 1.5× increase in naïve control. An increasing extracellular glutamate was also observed in both naïve and GAD65 transduced rats. FIG. 18A is a chart showing extracellular GABA concentration in the SN during STN stimulation in naïve rats (N=4). FIG. 18B is a chart showing extracellular GABA concentration in the SN during STN stimulation in rAAV-GAD rats (N=3) NB. ST1-2 min Low Freq Stim ST2-5 min Low Freq Stim.

FIG. 19A-F is a photograph showing AAV-GAD65 expression in vivo in naïve and GAD65 transduced animals. A,B,C, and D; GAD65 expression in the STN detected with GAD65 Ab (Boehringer). A and C; Naïve STN, showing endogenous GAD65 expression. B and D; rAAV-GAD65 transduced STN, an increase in cell bodies expressing GAD65 is seen. E and F; GAD65 expression in the hippocampus. E; naïve. F; rAAV-GAD65 transduced.

Example 7

In Vivo Primate Studies

Methods
i) Subjects

Seven Rhesus monkeys were housed at the Biological Research Laboratories at the University of Illinois. The monkeys were singly housed in quarters with a 12-hour light/dark cycle. The animals received food and water ad libitum. The study was performed in accordance with federal guidelines of proper animal care and with the approval of both Rush Presbyterian and University of Illinois Animal Care Committees.

TABLE 5

Subjects of the present study. D.O.B: date of birth. Weight corresponds to data obtained on the day of rAAV surgery (see Table 6 for experimental groups and Table 7 for progression of weight throughout the study)

| Monkey # | D.O.B. | Age | Sex | Weight | MPTP | MRI | rAAV Injection | Necropsy |
|---|---|---|---|---|---|---|---|---|
| 6436 | Jul-94 | 6 | M | 7.1 kg | Oct. 6, 1999<br>Nov. 18, 1999<br>Dec. 6, 1999 | May 24, 2000 | Sep. 29, 2000 | Jan. 10, 2001 |
| 6442 | Jul-94 | 6 | M | 8 kg | Oct. 6, 1999<br>Nov. 18, 1999<br>Dec. 6, 1999 | May 24, 2000 | Sep. 29, 2000 | Jan. 10, 2001 |
| 6474 | Apr-93 | 7 | M | 5.9 kg | Oct. 7, 1999<br>Nov. 18, 1999<br>Dec. 6, 1999 | May 24, 2000 | Sep. 29, 2000 | Jan. 10, 2001 |
| 6485 | Nov-94 | 5 | M | 6.1 kg | Oct. 7, 1999<br>Nov. 18, 1999<br>Dec. 6, 1999 | May 24, 2000 | Sep. 29, 2000 | Jan. 10, 2001 |
| 6446 | Jul-94 | 6 | M | 7.5 kg | Oct. 6, 1999<br>Nov. 18, 1999<br>Dec. 6, 1999 | May 24, 2000 | Sep. 29, 2000 | planned<br>Jun. 29, 2001 |
| 6469 | Feb-94 | 6 | M | 5.9 kg | Oct. 6, 1999<br>Nov. 18, 1999<br>Dec. 6, 1999 | May 24, 2000 | Sep. 29, 2000 | planned<br>Jun. 29, 2001 |

TABLE 5-continued

Subjects of the present study. D.O.B: date of birth. Weight corresponds to data obtained on the day of rAAV surgery (see Table 6 for experimental groups and Table 7 for progression of weight throughout the study)

| Monkey # | D.O.B. | Age | Sex | Weight | MPTP | MRI | rAAV Injection | Necropsy |
|---|---|---|---|---|---|---|---|---|
| 6482 | Feb-94 | 6 | M | 6.6 kg | Oct. 6, 1999<br>Nov. 18, 1999<br>Dec. 6, 1999 | May 24, 2000 | Sep. 29, 2000 | planned<br>Jun. 29, 2001 | ii) Behavioral Testing

Clinical Rating

A clinical rating scale (CR scale) was used monthly before and after MPTP administration to quantitatively assess the clinical status of the monkeys by using a previously validated measure (Kurlan, et al. (1991)) *Ann Neurol.* 29:677-9: (Kurlan, et al. (1991)) *Mov Disord.* 16:111-8. (Jagust, et al. (1997) *Ann N Y Acad Sci.* 826:254-62), (Emborg, et al. (1998) *J Comp Neurol.* 401:253-65). All the ratings were obtained from videotape records by a trained observer blind to the treatment conditions. The scale consists of ratings of tremor (0-3 for each arm), posture (0-2), gait (0-5), bradykinesia (0-5), balance (0-2), gross motor skills (0-4 for each arm), defense reaction (0-2) and freezing (0-2). The score was obtained as the sum of the features out of a total of 32 points, 0 corresponds to normal scoring and 32 to extreme severe disability. Occurrence of dyskinesias, psychological disturbances and vomiting was also recorded.

Activity Monitoring

Each monkey was tranquilized with ketamine (10 mg/kg, i.m.) and fitted with a primate vest that contained a PAM2 activity monitor (IM Systems, Baltimore, Md.; (Emborg, et al. (1998) *J Comp Neurol.* 401:253-65) in the inside back pocket. These monitors measure acceleration. Every time a monitor senses an acceleration that exceeds a threshold of 0.1 G, and electrical pulse is generated and recorded. Thus, each pulse represents 234 msec. of acceleration above the 0.1 G threshold. The number of pulses is expressed for a preselected time period (1 min.). After one week period, the animals were again tranquilized with ketamine (15 mg/kg, i.m.), the jacket was removed, the activity monitor interfaced with a Macintosh computer and the data was downloaded. The data was expressed as the mean of each 12 hour light/dark cycle.

iii) MRI Scanning (MRI)

All stereotaxic injections were performed under MRI guidance. The MRI scans were performed in a 1.5T Sigma Unit. The animals were anesthetized with telazol (4-6 mg/kg, im) for transportation and scanning. Atropine (0.02-0.04 mg/kg, s.c.) was also administered. Vital signs were monitored throughout the procedure and until waking up response. The animals were placed in a MRI-compatible stereotaxic frame. Head orientation coordinates were recorded in order to replicate the head position during surgery. T1 and T2 weighed images were obtained, as well as a 3D reconstruction with 1 mm thickness slices. The coronal zero was identified by the location of ear bars that were filled with vegetable oil.

iii) Surgical Procedures

MPTP Treatment

Intracarotid injections of MPTP were performed according to our previously published protocols (Kordower, et al. (1994) *Proc Natl Acad Sci USA.* 91:10898-902), (Emborg and Colombo (1994) *Mol Chem Neuropathol.* 21:75-82), ((Emborg, et al. (1998) *J Comp Neurol.* 401:253-65)). The monkeys were first tranquilized with ketamine (10 mg/kg, i.m.) and then anesthesia was induced and maintained with isofluorane (1-2%). Each animal received prophylactic antibiotic treatment previous to the incision (cefazolin 25 mg/kg i.v.). The animals were positioned in the supine position with neck hyperextended and slightly turned left. Under sterile conditions a number 15 blade was used to cut through the skin along the medial edge of the esternocleidomastoide muscle. The carotid sheath were opened using fine iris scissors and the common carotid artery, internal jugular vein and vagus nerves identified. The common carotid were exposed below the carotid bifurcation. Silk (2.0) thread was looped around the common carotid artery while the external carotid artery was identified with the superior thyroid artery seen branching distal to the bifurcation and clamped. A 27-G butterfly needle was inserted into the common carotid artery in a direction retrograde to the direction of the blood flow, and 20 ml of saline containing 3 mg of MPTP-HCL was infused at a rate of 1.33 ml/min. (15 min.). After the infusion was completed, a 3 ml post-flush of saline was delivered. The needle was withdrawn from the carotid artery, and a small piece of Gelfoam was used to apply focal pressure to the penetrated vessel. The musculature, SC tissues and skin were then closed in a routine fashion. Buprenex (0.01 mg/kg. i.m.) was given upon waking up response and 24 hours post surgery.

rAAV Injections

At least 6 months post last unilateral intracarotid MPTP administration (see Table 6) the animals received AAV intracerebral injections. Monkeys were intubated and anesthetized with isofluorane (1-2%). The monkeys were placed in the stereotaxic frame in the same orientation used during the MRI scans. Under sterile conditions, a coronal incision was made over the scalp. Entry point was identified according to its distance from the MRI-calculated zero mark, then an entry hole was drilled. The exposure of the superior sagittal sinus served as the midline zero. Before loading the vector in the syringe, a 20% solution of mannitol was drawn. The vector was drawn after vortexing the vial for few seconds before injection. The vector was combined in a proportion of 1 part virus+½ part mannitol 20% (e.g: 10 µl AAV+5 µl mannitol). Measurement of cortical surface was recorded and the Hamilton syringe was lowered to the target. The infusion of the vector was performed with an infusion pump attached to the stereotaxic micromanipulator. The rate of infusion was 1.0 µl/min. After the injection was completed, we waited 3 minutes before retrieving the syringe. The needle gauge was: 22S (25 µl and 50 µl syringes according to final total volume, models 1701 and 1705 Hamilton syringes with removable needles and teflon tip plungers). The target was the subthalamic nucleus, ipsilateral to the intracarotid MPTP infusion. Identical infusion procedures were employed for experimental and control animals. Following the injections, the burr holes were filled with Gelfoam and the skin was closed in anatomical layers. Analgesics (buprenex, 0.01 mg/kg i.m.)

were administered upon waking up response and 24 hours post surgery. Prophylactic antibiotic treatment was avoided to prevent possible interaction with lentiviral transfection.

TABLE 6

Stereotaxic coordinates (based on MRI measurements) and experimental groups. Injection site: right subthalamic nucleus. AP 0 corresponds to the MRI image where the ear bars of the stereotaxic frame were present. ML 0 corresponds to the sagittal sinus.

| Monkey # | 6436 | 6442 | 6446 | 6469 | 6474 | 6482 | 6485 |
|---|---|---|---|---|---|---|---|
| rAAV Vector | GFP | GFP | GAD65 | GAD65 | GAD65 | GAD67 | GAD67 |
| Vector Volume | 10 µl | 10 µl | 20 µl | 10 µl | 10 µl | 10 µl | 10 µl |
| Mannitol Volume | 5 µl | 5 µl | 10 µl | 5 µl | 5 µl | 5 µl | 5 µl |
| ANTEROSTERIOR(AP) | 12 | 13 | 12 | 9 | 10 | 12 | 12 |
| MEDIOLATERAL (ML) | 7 | 8 | 9 | 8 | 7 | 5 | 6 |
| DORSOVENTRAL(DV) | 29 | 28 | 25 | 31 | 28 | 30 | 32 |
| MRI-AP 0 | S 1.1 | S 0.9 | S 2.3 | S 1.1 | S 1.4 | I 0.4 | S 1.6 | iv) Necropsy, Preparation of Tissue

Three months rAAV infusions, 4 monkeys (see Table 5) were anesthetized with pentobarbital (25 mg/kg, iv.) and perfused transcardially (previous intraventricular injection of 1 ml of heparin) with normal saline (300 ml) followed by 4% Zamboni's fixative (400 ml). The brains were then immersed in a 4% Zamboni's fixative for 48 hours of post-fixation, cryoprotected by immersion in a graded (10-40%) sucrose/0.1 M phosphate buffered saline (PBS, pH 7.2) solution. The brains were cut frozen (40 µm) on a sliding knife microtome. All the sections were stored in a cryoprotectant solution before processing.

Samples of fluids and tissue were obtained for analysis of unspecific side effects or propagation of viral particles. Serum samples were obtained previous to necropsy procedure. Before Zamboni's fixative was perfused samples of heart, liver, kidney, striate muscle and testicle were obtained and immediately frozen for posterior PCR analysis of AAV presence. Additional kidney and liver samples were obtained and postfixated in Zamboni's for histhopathology.

v) Immunohistochemistry

Sections through midbrain and striatum were used for immunohistochemical staining of TH and GAD according to our previously published protocol. Endogenous peroxidase activity was removed with a 20 minute incubation in 0.1 M sodium periodate. After 3×10 minute washes in PBS plus 0.05% Triton-X (dilution media) background staining were blocked with a 1 hour incubation in a Tris buffered saline solution containing 3% normal horse serum, 2% bovine serum albumin, and 0.05% Triton X-100. The sections were then incubated with a monoclonal TH (1:20,000); Chemicon Inc., CA) primary antibody for 48 hours at room temperature. Sections were then incubated for 1 hour in horse antimouse (TH) biotinylated secondary antibodies (1:100; Vector Laboratories, Burlingame, Calif.). After 12×10 minute washes in dilution media, the sections were placed in the avidin biotin (ABC, "Elite" kit, Vector Laboratories) substrate (1:1,000) for 75 minutes. sections were then washed in a 0.1 M imidazole/1.0 M acetate buffer, pH 7.4, and then reacted in a chromagen solution containing 0.05% 3,3'-diaminobenzidine, and 0.05% $H_2O_2$.

Controls consisted of processing tissue in an identical manner except for by using the primary antibody solvent or an irrelevant immunoglobulin G (IgG) in lieu of the primary antibody. sections were mounted on gelatin-coated slides, dehydrated, and coverslipped with Permount.

Additional sections were mounted and coverslipped with DPX for observation of GFP fluorescence with ultraviolet light.

Results i) General Observations

All animals tolerated the MPTP lesion and AAV injections without complications. The animals increased or maintained their weight throughout the study and did not display evidence of nausea, vomiting, diarrhea, signs of weakness, fever or infection. Throughout the study, they were cooperative during test sessions and responsive to food stimuli (See Table 7 below).

TABLE 7

Animal weights throughout the course of the study. The sac/present weight column corresponds to the weight at the time of sacrifice for monkeys 6436, 6442, 6474 and 6485. Animals 6446, 6469 and 6482 remain alive.

| Monkey # | Last MPTP surgery (Kg.) | rAAV surgery (Kg.) | sac/present (Kg.) |
|---|---|---|---|
| 6436 | 6 | 7.1 | 7.2 |
| 6442 | 7.1 | 8 | 8.4 |
| 6474 | 5.2 | 5.9 | 6.6 |
| 6485 | 4 | 6.1 | 6.1 |
| 6446 | 6.5 | 7.5 | 7.4 |
| 6469 | 5.9 | 5.9 | 6.9 |
| 6482 | 5.1 | 6.6 | 7.2 | ii) Clinical Rating

Prior to the administration of MPTP all the animals displayed behavior indicative of normal young adult male Rhesus monkeys. They were fast with steady movements and did not show any neurological impairment. As assessed using the rating scale, all the animals scored 0 in the pre-MPTP condition. There were no changes in clinical rating scores during the two weeks period prior to MPTP treatment.

After the intracarotid MPTP infusion, there was significant variability in the parkinsonian status of the animals and to further their motor impairments ice. MPTP infusions were repeated. After the third MPTP some animals appeared mildly hemiparkinsonian, while one animal in particular (6474) appeared severely hemiparkinsonian, presenting tremor, flexed posture and impaired motor skills in the hand contralateral to the infusion, as well as balance disturbance, stooped posture, bradykinesia and slow spontaneous circling ipsilateral to the lesion side (see Table 8).

The animals recovered from the rAAV surgery uneventfully. Two monkeys showed moderate improvement in their clinical score. Interestingly, 6446 that received the highest total volume of vector and mannitol improved his score.

Another monkey, 6485 also showed some improvement. The rest of the animals did not show significant changes.

TABLE 8

Clinical Rating Score

| Treatment | Monkey # | Pre | Post 1 | Post 2 | Post 3 |
|---|---|---|---|---|---|
| GFP | 6436 | 7.5 | 7.5 | 8 | 7.5 |
|  | 6442 | 8 | 6.5 | 7 | 7 |
| GAD65 20 + 10 | 6446 | 7.5 | 7.5 | 5 | 5.5 |
| GAD65 10 + 5 | 6469 | 5.5 | 4.5 | 5.5 | 5.5 |
|  | 6474 | 11 | 10 | 11.5 | 10 |
| GAD67 10 + 5 | 6482 | 5.5 | 4 | 5 | 5 |
|  | 6485 | 6.5 | 4 | 4 | 4.5 | iii) Activity

Figure 19A:
FIG. 19A-19F are microphotographs showing rAAV-GAD65 expression in vivo.
Figure 19B:
Figure 19C:
Figure 19D:
Figure 19E:
Figure 19F:
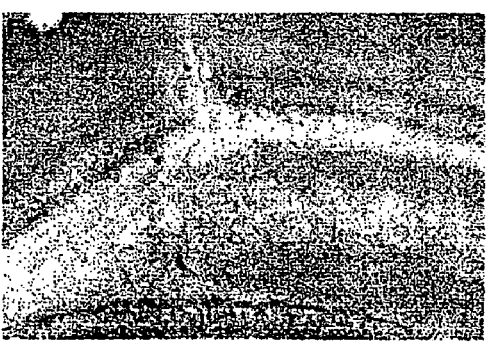
Figure 20A:
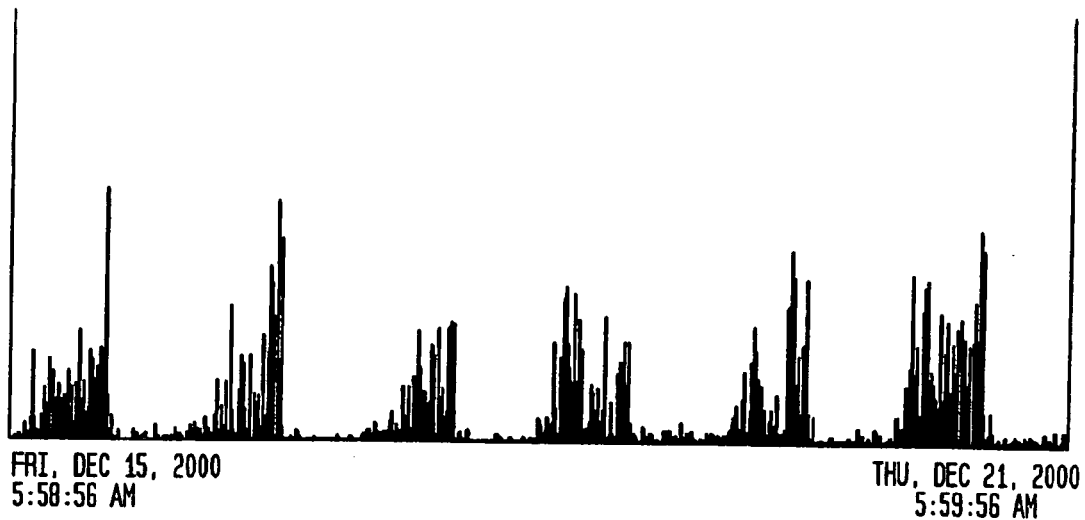
FIGS. 20A and 20B are rasterplots showing activity in a monkey before GAD67 treatment, respectively.
Figure 20B:
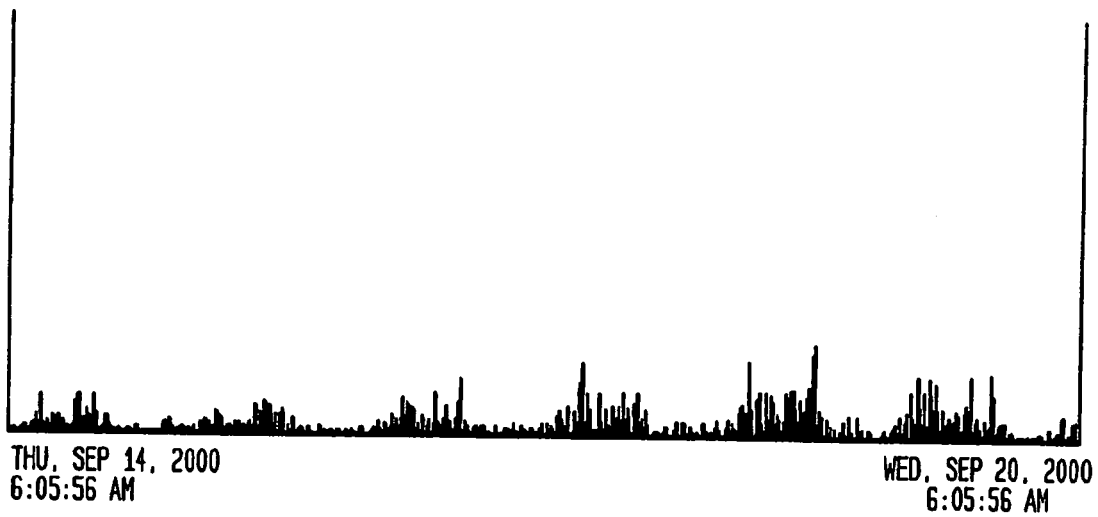

Prior to any treatment, spontaneous general activity levels in the home cage measured with personal activity monitors located in primate jackets were similar to what was observed in previous studies. As observed in the clinical rating, after MPTP treatment the animals presented variable activity levels during the day. FIGS. 20A and 19B are rasterplots showing activity before (A) and after (B) GAD67 treatment (monkey 6482). Observe the presence of hills and valleys corresponding to the activity during the day and night respectively. In all the cases, a circadian rhythm was observed and remained unaffected after AAV surgery (FIG. 20).

In general, the animals' activity during the day decreased after MPTP treatment. After AAV surgery, the activity of two animals that received GAD67 was increased (Table 9).

TABLE 9

Activity recorded with personal monitors.

| Treatment | Monkey # | Pre |  | Post 1 |  | Post 2 |  | Post 3 |  |
|---|---|---|---|---|---|---|---|---|---|
|  |  | Mean | SE | Mean | SE | Mean | SE | Mean | SE |
| DAY |  |  |  |  |  |  |  |  |  |
| GFP | 6436 | 7.17 | 2.09 | 7.93 | 1.01 | 7.14 | 1.54 | 7.54 | 0.46 |
|  | 6442 | 29.65 | 9.9 | 18.45 | 5.13 | 14.61 | 0.47 | 13.24 | 0.78 |
| GAD65 20 + 10 | 6446 | 5.94 | 0.75 | 4.96 | 0.51 | 6.32 | 1.07 | 4.13 | 0.47 |
| GAD65 10 + 5 | 6469 | 12.45 | 2.14 | 11.5 | 3.02 | 10.83 | 3.43 | 12.74 | 1.72 |
|  | 6474 | 13.96 | 2.71 | 13.16 | 1.25 | 10.22 | 0.99 | 7.61 | 1.43 |
| GAD67 10 + 5 | 6482 | 8.23 | 1.67 | 5.63 | 0.98 | 5.78 | 1.17 | 25.89 | 1.71 |
|  | 6485 | 21.17 | 6.13 | 28.24 | 0.96 | 46.72 | 2.61 | 32.61 | 1.49 |
| NIGHT |  |  |  |  |  |  |  |  |  |
| GFP | 6436 | 3.91 | 1.03 | 2 | 0.48 | 2.19 | 0.25 | 2.26 | 0.16 |
|  | 6442 | 3.85 | 0.33 | 4.29 | 1.47 | 3.18 | 0.16 | 2.5 | 0.2 |
| GAD65 20 + 10 | 6446 | 1.12 | 0.33 | 1.3 | 0.1 | 1.9 | 0.36 | 0.71 | 0.11 |
| GAD65 10 + 5 | 6469 | 2.7 | 0.69 | 3.02 | 0.82 | 2.7 | 0.65 | 2.2 | 0.76 |
|  | 6474 | 2.5 | 0.31 | 3.18 | 0.76 | 2.17 | 0.15 | 1.43 | 0.09 |
| GAD67 10 + 5 | 6482 | 3.07 | 0.67 | 2.06 | 0.34 | 1.76 | 0.19 | 4.5 | 0.66 |
|  | 6485 | 1.29 | 0.59 | 0.68 | 0.02 | 0.64 | 0.11 | 0.59 | 0.09 | iv) TH Immunostaining

Sections through the midbrain showed varying degrees of degeneration of TH-immunoreactive neurons within the substantia nigra pars compacta ipsilateral to the intracarotid MPTP infusion. Rhesus 6474, displayed a comprehensive loss of TH-ir neurons within the central and ventrolateral portions of the A9 region while A10 ventral tegmental area was minimally affected. In addition, severe loss of TH-ir positive fibers in the caudate and putamen was also observed. Three of the 4 animals (Rh # 6436, 6442, 6482) displayed minimal neuronal degeneration within the substantia nigra pars compacta as well as a mild decrease of TH immunostaining in the striatum ipsilateral to the side of MPTP intracarotid infusion.

Figure 21A:
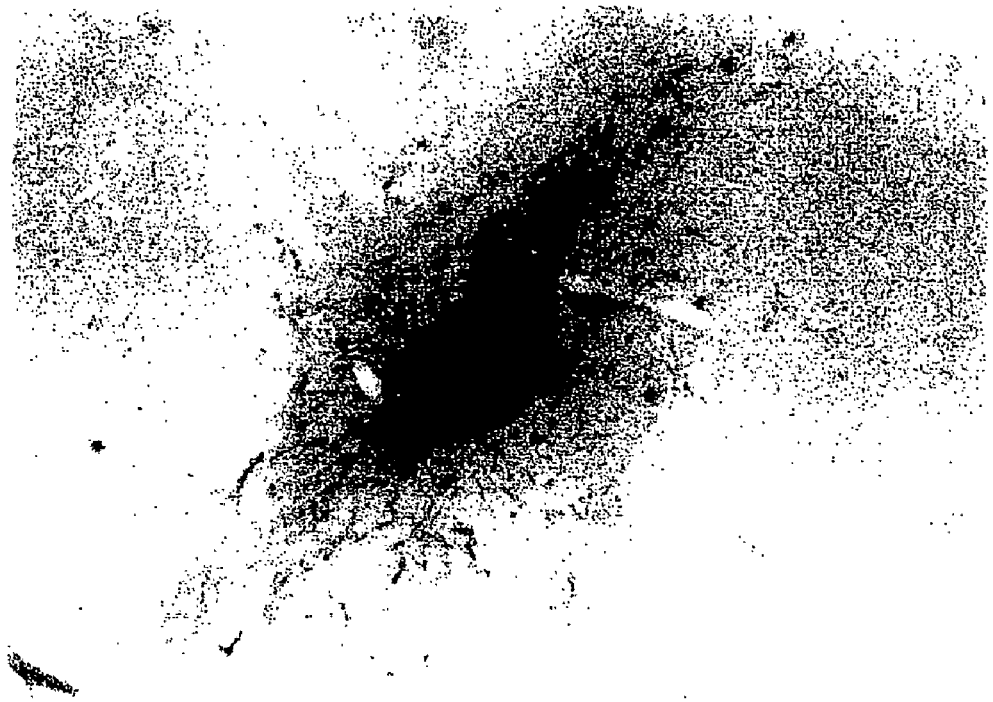
FIGS. 21A and 21B are microphotographs showing GFP immunostaining at an injection site. Neuronal-like cells stained with GFP antibody are shown in 21A and glial-like cells stained with GFP antibody are shown in 21B.
Figure 21B:
Figure 22:
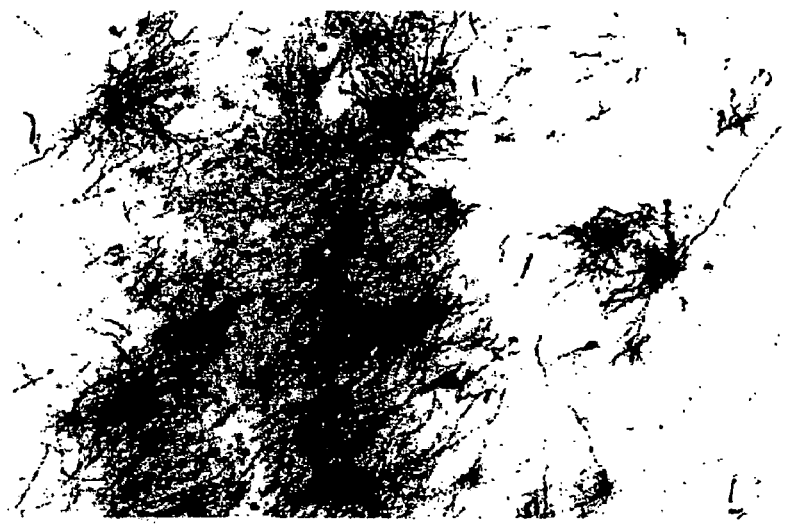
FIG. 22 is a more detailed image of GFP immunostaining at an injection site.

These findings corresponded to the data obtained with the clinical ratings scale, e.g. Rh 6474 presented severe parkinsonism (higher score in the rating scale) and had the most extensive loss of TH positive cells and fibers in the nigrostriatal system.

v) GFP Immunoflourescence rAAV-GFP treated monkeys (6436 and 6442) presented GFP positive cells limited to the subthalamic nucleus ipsilateral to the rAAV injection. The cell bodies were easily identified and limited in number to 6-10 positive neuron-like cells per animal. In contrast, no monkeys receiving rAAV-GAD presented GFP positive cells. FIGS. 21A and 21B are photographs of GFP immunostaining at injection site (GFP antibody from Clontech Palo Alto Calif.), showing neuronal-like cells stained with GFP antibody in (A), while glial-like cells stained with GFP antibody are shown in (B) FIG. 22 is a more detailed image of GFP immunostaining at injection site.

vi) GAD Immunostaining rAAV-GFP and rAAV-GAD treated animals did not show signs of anatomical disruption in the area of injection and the neurons presented a normal morphology. In the rAAV-GFP treated animals (6442 and 6436) GAD was observed where is normally found in areas such as the substantia nigra pars reticulata, striatum, thalamus and cerebral cortex. The immunostaining did not show differences between the AAV-GFP treated side and the untreated one.

Figure 23:
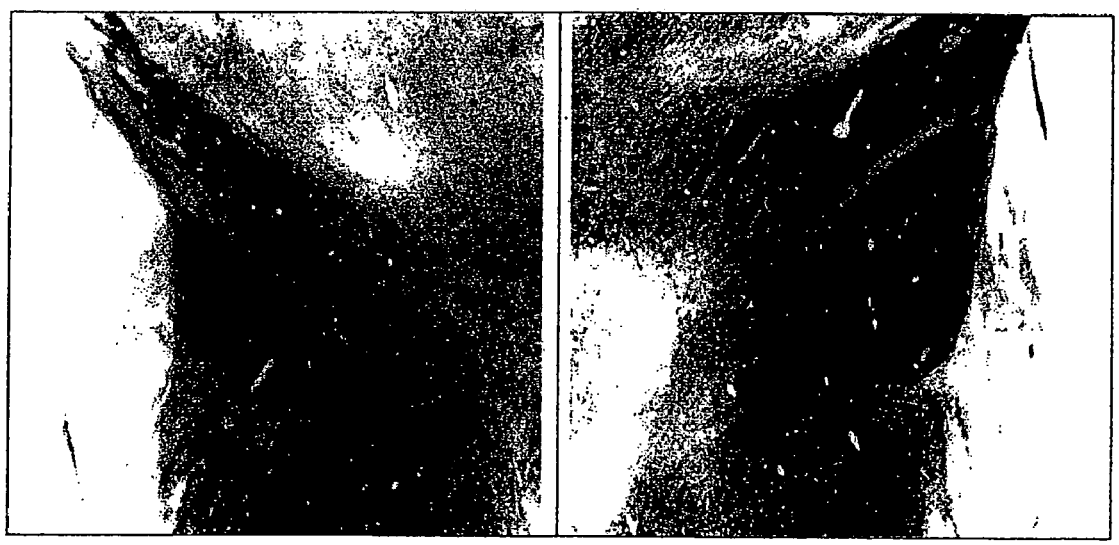
FIG. 23 is a photograph of GAD immunostaining on rAAV-GAD treated monkey, showing an increase in immunostaining on the rAAV-GAD treated side on the right while the morphology of the region remained unaltered after surgery.

In comparison, rAAV-GAD treated animals showed increase GAD staining in the subthalamic nucleus ipsilateral to the AAV injection. Rh 6474 (GAD65) presented only a mild increase of GAD positive fibers. However, Rh 6485 (GAD67) displayed robust expression of GAD distributed throughout the neuropil of the subthalamic and immediately adjacent area. FIG. 23 is a photograph of GAD immunostaining on rAAV-GAD treated monkey. There is an increase in immunostaining on the rAAV-GAD treated side on the right. The morphology of the region remained unaltered after surgery.

The experimental results appear to demonstrate that the MPTP lesion induced in most of the animals a mild parkinsonian syndrome. In three of the four animals that underwent postmortem evaluation, the dopaminergic marker TH revealed minimal neuronal degeneration within the substantia nigra pars compacta as well as a mild decrease of TH immunostaining in the striatum ipsilateral to the side of MPTP intracarotid infusion.

The AAV surgery did not further impair the animals. The monkeys maintained or increased their body weight throughout the study, their circadian rhythm remained intact (as measured by the activity monitors) and the animals did not show signs of unspecific neurological dysfunction, or infection.

Behaviorally, 6446 (GAD65 20+10) 6485 (GAD67 10+5) showed moderate improvements in their Parkinsonian signs as measured by the clinical rating scale. The activity increased in the two animals that received GAD67. Histologically, only rAAV-GFP monkeys presented GFP immunofluorescence in 6-10 cells, in the subthalamic nucleus ipsilateral to the rAAV injection. rAAV-GAD treated animals displayed mild to strong increase GAD expression in the subthalamic nucleus Collectively, these results demonstrate the phenotypic correction of Parkinsonian rats following stereotactic injection of rAAV expressing glutamic acid decarboxylase 65 and 67 into the subthalamic nucleus. Hemiparkinsonian rats were generated by unilateral 6-hydroxydopamine (6-OHDA) lesioning of the median forebrain bundle. The 6-OHDA lesion induced ipsilateral bias in head position and rotational asymmetry, as well as forepaw touching and locomotor activity decreasing were used as quantitative markers of the PD phenotype. In order to inhibit STN activity, high titer recombinant AAV vectors expressing human glutamic acid decarboxylase (GAD65/67) were generated and stereotactically injected into ipsilateral STN. Expression of the transgenic human GAD65/67 mRNA and proteins were detected by real time quantitive RT-PCR and immunocytochemistry. Using in vivo microdialysis, the extracellular GABA and glutamate in the SN in response to STN low frequency stimulation (STN-LFS) was evaluated. In chronically (aged) PD rats administered rAAVGAD65/67 intraSTN, rotational asymmetry was alleviated and forepaw touching and locomotor activity were improved. Of interest, in rats administered rAAVGAD65/67 vectors into the STN prior to the MFB 6-OHDA lesion, all asymmetries were markedly improved with the behavioral phenotype approaching those of normal animals. Microdialysis data also show a significant increase of extracellular GABA in GAD transduced rats compared to normal rats following STN-LFS. These results suggest that transduction of GAD isoforms into the STN using rAAV vector can inhibit the overactivity of target neurons in PD rats and may provide for strong protection against neurotoxic insults to dopaminergic neurons.

Example 8

GAD65 Transduction of the Subthalamic Nucleus Changes the Action of Excitatory Projections to the Substantia Nigra This example demonstrates the change in excitatory projections to the substantia nigra (STN). The subthalamic nucleus has a prominent excitatory connection with the substantia nigra (SN). In Parkinson's disease, overactivity in the STN leads to progressive degeneration of dopamine neurons in the SN, as well as the common features of Parkinsonism such as tremor, rigidity and bradykinesia.

The SN of normal rats and rats treated with the recombined associate adenovirus (rAAV) containing the gene for human glutamic acid decarboxylase 65 (rAAV CBA-hGAD65), which converts glutamate to GABA in neurons were used to perform extracellular electrophysiology and microdialysis. The medial forebrain bundle was lesioned after the virus was injected into the STN to model PD.

Results from extracellular recordings of the SN during STN stimulation in normal rats (n=4) revealed 78% (n=14/19 neurons) excitatory responses, 5% (n=1/19) inhibitory, and 21% (n=4/19) had no response. In GAD transduced rats (n=5), the results showed 17% (n=3/18 neurons) with excitatory responses, 78% (n=14/18) with inhibitory and 5% (n=118) had no response. Microdialysis experiments detected a 4.4× increase in mean GABA concentration in the SN of GAD transduced rats (n=4) during low frequency (10 Hz, 5') electrical stimulation of the STN, compared to a 1.5× increase in control rats (n=3).

These experiments demonstrate that GAD transduction of neurons in the STN increases inhibition in the SN and decreases the excitatory effect of STN stimulation on neurons in the SN which may alleviate the symptoms of PD. This demonstrates that changing the excitatory projection from the STN to the SN into an inhibitory projection, using a gene therapy approach, alleviates the symptoms of PD.

What is claimed is:

1. A method of ameliorating a symptom of a neurodegenerative disorder by altering expression of glutamic acid decarboxylase 65 ($GAD_{65}$) in a region of the brain of a subject having a neurodegenerative disorder comprising:
   identifying a target site in the brain that requires modification;
   delivering an adeno-associated viral (AAV) vector comprising a nucleotide sequence encoding glutamic acid decarboxylase 65 ($GAD_{65}$) directly to the target site in the brain; and
   expressing $GAD_{65}$ in the target site, thereby ameliorating at least one symptom of the neurodegenerative disorder.

2. The method of claim 1, wherein the AAV vector is delivered using stereotaxic delivery.

3. The method of claim 1, wherein the region of the brain is selected from the group consisting of basal ganglia, subthalamic nucleus (STN), pedunculopontine nucleus (PPN), substantia nigra (SN), thalamus, hippocampus, cortex, and combinations thereof.

4. The method of claim 1, wherein the region of brain is the subthalamic nucleus (STN).

5. The method of claim 1, wherein the neurodegenerative disorder is Parkinson's disease.

6. A method of ameliorating a symptom of a neurodegenerative disorder by altering expression of glutamic acid decarboxylase 65 (GAD$_{65}$) in a region of the brain of a subject having a neurodegenerative disorder which causes morphological and/or functional abnormality of a neural cell or population of neural cells comprising:

identifying a target site in the brain that requires modification;

delivering an AAV vector comprising a nucleotide sequence encoding glutamic acid decarboxylase 65 (GAD$_{65}$) directly to the target site in the brain; and expressing GAD$_{65}$ in the target site, thereby ameliorating at least one symptom of the neurodegenerative disorder.

7. The method of claim 6, wherein the AAV vector is delivered using stereotaxic delivery.

8. The method of claim 6, wherein the region of the brain is selected from the group consisting of basal ganglia, subthalamic nucleus (STN), pedunculopontine nucleus (PPN), substantia nigra (SN), thalamus, hippocampus, cortex, and combinations thereof.

\* \* \* \* \*

SEQUENCE LISTING

<160> NUMBER OF SEQ ID NOS: 17

<210> SEQ ID NO 1
<211> LENGTH: 29
<212> TYPE: DNA
<213> ORGANISM: Homo sapiens

<400> SEQUENCE: 1
atatatctcg agatggcatc tcggggctc                              29

<210> SEQ ID NO 2
<211> LENGTH: 33
<212> TYPE: DNA
<213> ORGANISM: Homo sapiens

<400> SEQUENCE: 2
gcgcgcgaat tcttataaat cttgtccaag gcg                         33

<210> SEQ ID NO 3
<211> LENGTH: 28
<212> TYPE: DNA
<213> ORGANISM: Homo sapiens

<400> SEQUENCE: 3
tatatctcga gatggcgtct tcgaccca                               28

```
<210> SEQ ID NO 4
<211> LENGTH: 29
<212> TYPE: DNA
<213> ORGANISM: Homo sapiens

<400> SEQUENCE: 4
cagctgaatt cttacagatc ctggcccag                                    29

<210> SEQ ID NO 5
<211> LENGTH: 47
<212> TYPE: DNA
<213> ORGANISM: Homo sapiens

<400> SEQUENCE: 5
gttttgggac gtttcctgag tcaggtgagt ctatgggacc cttgatg                47

<210> SEQ ID NO 6
<211> LENGTH: 40
<212> TYPE: DNA
<213> ORGANISM: Homo sapiens

<400> SEQUENCE: 6
cagttttccg cgaatctgtg ggaggaagat aagaggtatg                        40

<210> SEQ ID NO 7
<211> LENGTH: 30
<212> TYPE: DNA
<213> ORGANISM: adeno-associated virus 2

<400> SEQUENCE: 7
ccgtggccga gaagctgcag cgcgactttc                                   30

<210> SEQ ID NO 8
<211> LENGTH: 47
<212> TYPE: DNA
<213> ORGANISM: adeno-associated virus 2

<400> SEQUENCE: 8
catcaagggt cccatagact cacctgactc aggaaacgtc ccaaaac                47

<210> SEQ ID NO 9
<211> LENGTH: 44
<212> TYPE: DNA
<213> ORGANISM: Homo sapiens

<400> SEQUENCE: 9
ccaccaccac caaagcccgc aggtgagtct atgggaccct tgat                   44

<210> SEQ ID NO 10
<211> LENGTH: 45
<212> TYPE: DNA
<213> ORGANISM: Homo sapiens

<400> SEQUENCE: 10
cctgctgtcg tccttatgcc gctctgtggg aggaagataa gaggt                  45

<210> SEQ ID NO 11
<211> LENGTH: 30
<212> TYPE: DNA
<213> ORGANISM: adeno-associated virus 2

<400> SEQUENCE: 11
agtctctaga gtcctgtatt agaggtcacg                                   30
```

```
<210> SEQ ID NO 12
<211> LENGTH: 44
<212> TYPE: DNA
<213> ORGANISM: adeno-associated virus 2

<400> SEQUENCE: 12
atcaagggtc ccatagactc acctgcgggc tttggtggtg gtgg            44

<210> SEQ ID NO 13
<211> LENGTH: 45
<212> TYPE: DNA
<213> ORGANISM: adeno-associated virus 2

<400> SEQUENCE: 13
acctcttatc ttcctcccac agagcggcat aaggacgaca gcagg            45

<210> SEQ ID NO 14
<211> LENGTH: 30
<212> TYPE: DNA
<213> ORGANISM: adeno-associated virus 2

<400> SEQUENCE: 14
cgggtgacgt agtagtctag agcatggaaa            30

<210> SEQ ID NO 15
<211> LENGTH: 18
<212> TYPE: DNA
<213> ORGANISM: Woodchuck hepatitis virus

<400> SEQUENCE: 15
tggcgtggtg tgcactgt            18

<210> SEQ ID NO 16
<211> LENGTH: 18
<212> TYPE: DNA
<213> ORGANISM: Woodchuck hepatitis virus

<400> SEQUENCE: 16
gttccgccgt ggcaatag            18

<210> SEQ ID NO 17
<211> LENGTH: 22
<212> TYPE: DNA
<213> ORGANISM: Woodchuck hepatitis virus

<400> SEQUENCE: 17
tccgggactt tcgctttccc cc            22
```